(12) United States Patent
Werneth et al.

(10) Patent No.: US 8,617,156 B2
(45) Date of Patent: Dec. 31, 2013

(54) LOW POWER TISSUE ABLATION SYSTEM

(75) Inventors: Randell L. Werneth, San Diego, CA (US); Christopher G. Kunis, San Diego, CA (US); J. Christopher Flaherty, Topsfield, MA (US); Marshall L. Sherman, Cardiff by the Sea, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 336 days.

(21) Appl. No.: 12/340,414

(22) Filed: Dec. 19, 2008

(65) Prior Publication Data

US 2009/0182325 A1 Jul. 16, 2009

Related U.S. Application Data

(63) Continuation of application No. 11/484,878, filed on Jul. 11, 2006.

(60) Provisional application No. 60/698,355, filed on Jul. 11, 2005.

(51) Int. Cl.
*A61B 18/14* (2006.01)

(52) U.S. Cl.
USPC .............................................. 606/41; 606/45

(58) Field of Classification Search
USPC ..................................................... 606/32–45
See application file for complete search history.

(56) References Cited

U.S. PATENT DOCUMENTS

| 5,230,349 | A | * | 7/1993 | Langberg ....................... 607/122 |
| 5,313,943 | A | * | 5/1994 | Houser et al. ................. 600/374 |
| 5,893,848 | A | | 4/1999 | Negus et al. |
| 5,967,976 | A | * | 10/1999 | Larsen et al. ................. 600/374 |
| 5,971,980 | A | | 10/1999 | Sherman |
| 6,006,755 | A | * | 12/1999 | Edwards ....................... 128/898 |
| 6,030,379 | A | * | 2/2000 | Panescu et al. ................. 606/34 |
| 6,071,282 | A | | 6/2000 | Fleischman |
| 6,086,584 | A | * | 7/2000 | Miller ............................ 606/41 |
| 6,165,172 | A | * | 12/2000 | Farley et al. ..................... 606/33 |
| 6,235,024 | B1 | | 5/2001 | Tu |
| 6,325,798 | B1 | * | 12/2001 | Edwards et al. ................. 606/41 |
| 6,346,104 | B2 | | 2/2002 | Daly et al. |
| 6,558,378 | B2 | | 5/2003 | Sherman et al. |

* cited by examiner

*Primary Examiner* — Linda Dvorak
*Assistant Examiner* — Amanda Scott
(74) *Attorney, Agent, or Firm* — Christopher & Weisberg, P.A.

(57) ABSTRACT

Devices, systems and methods are disclosed for the ablation of tissue. Embodiments include an ablation catheter that has an array of ablation elements attached to a deployable carrier assembly. The carrier assembly can be constrained within the lumen of a catheter, and deployed to take on an expanded condition. The carrier assembly includes multiple electrodes that are configured to ablate tissue at low power. Additional embodiments include a system that includes an interface unit for delivering one or more forms of energy to the ablation catheter.

28 Claims, 7 Drawing Sheets

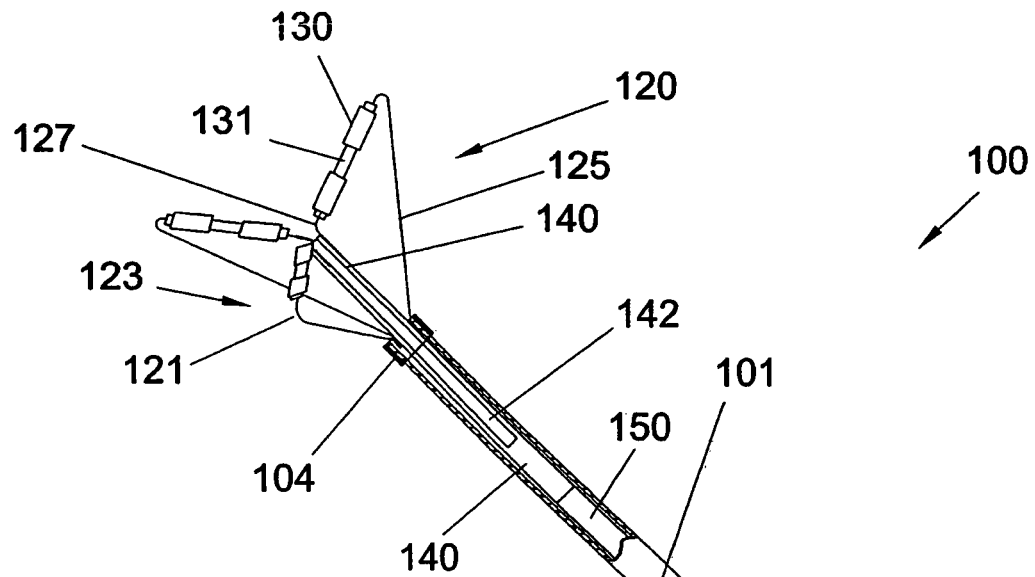
Fig. 4
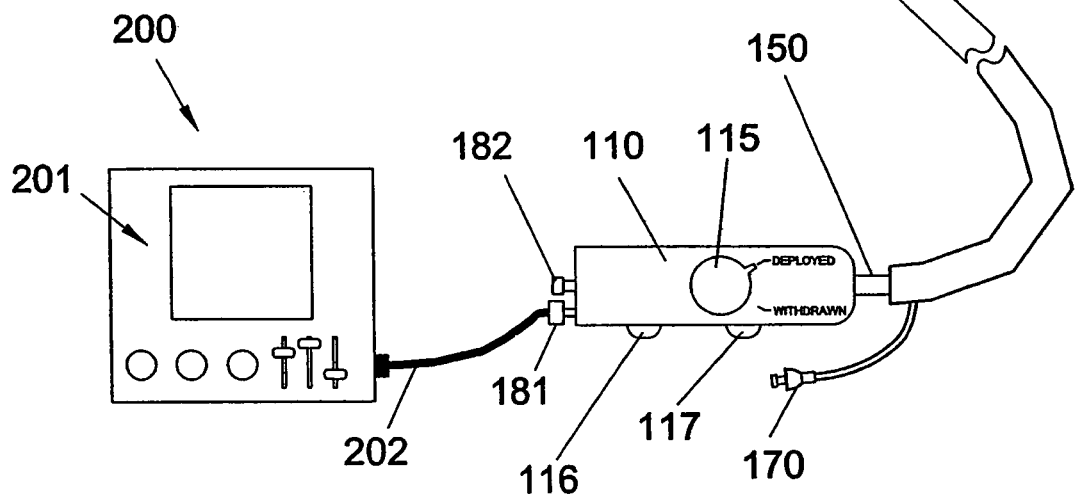
Fig. 4a
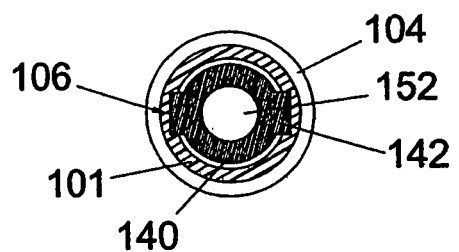

LOW POWER TISSUE ABLATION SYSTEM

CROSS-REFERENCE TO RELATED APPLICATIONS

This application is a continuation of pending U.S. application Ser. No. 11/484,878, filed Jul. 11, 2006; which application claims the benefit of U.S. Provisional Patent Application No. 60/698,355, filed Jul. 11, 2005; which applications are incorporated by reference in their entirety as if fully set forth herein.

FIELD OF THE INVENTION

The present invention relates generally to systems, catheters and methods for performing targeted tissue ablation in a subject. In particular, the present invention provides devices comprising one or more elements designed to efficiently deliver energy to tissue with precise control of the tissue to be ablated.

BACKGROUND OF THE INVENTION

Tissue ablation is used in numerous medical procedures to treat a patient. Ablation can be performed to remove undesired tissue such as cancer cells. Ablation procedures may also involve the modification of the tissue without removal, such as to stop electrical propagation through the tissue in patients with an arrhythmia. Often the ablation is performed by passing energy, such as electrical energy, through one or more electrodes causing the tissue in contact with the electrodes to heat up to an ablative temperature. Ablation procedures can be performed on patients with atrial fibrillation by ablating tissue in the heart.

Mammalian organ function typically occurs through the transmission of electrical impulses from one tissue to another. A disturbance of such electrical transmission may lead to organ malfunction. One particular area where electrical impulse transmission is critical for proper organ function is in the heart. Normal sinus rhythm of the heart begins with the sinus node generating an electrical impulse that is propagated uniformly across the right and left atria to the atrioventricular node. Atrial contraction leads to the pumping of blood into the ventricles in a manner synchronous with the pulse.

Atrial fibrillation refers to a type of cardiac arrhythmia where there is disorganized electrical conduction in the atria causing rapid uncoordinated contractions that result in ineffective pumping of blood into the ventricle and a lack of synchrony. During atrial fibrillation, the atrioventricular node receives electrical impulses from numerous locations throughout the atria instead of only from the sinus node. This condition overwhelms the atrioventricular node into producing an irregular and rapid heartbeat. As a result, blood pools in the atria and increases the risk of blood clot formation. The major risk factors for atrial fibrillation include age, coronary artery disease, rheumatic heart disease, hypertension, diabetes, and thyrotoxicosis. Atrial fibrillation affects 7% of the population over age 65.

Atrial fibrillation treatment options are limited. Three known treatments, lifestyle change, medical therapy and electrical cardioversion all have significant limitations. Lifestyle change only assists individuals with lifestyle-related atrial fibrillation. Medication therapy assists only in the management of atrial fibrillation symptoms, may present side effects more dangerous than atrial fibrillation, and fail to cure atrial fibrillation. Electrical cardioversion attempts to restore sinus rhythm but has a high recurrence rate. In addition, if there is a blood clot in the atria, cardioversion may cause the clot to leave the heart and travel to the brain or to some other part of the body, which may lead to stroke. What are needed are new methods for treating atrial fibrillation and other conditions involving disorganized electrical conduction.

Various ablation techniques have been proposed to treat atrial fibrillation, including the Cox-Maze procedure, linear ablation of various regions of the atrium, and circumferential ablation of pulmonary vein ostia. The Cox-Maze procedure and linear ablation procedures are unrefined, unnecessarily complex, and imprecise, with unpredictable and inconsistent results and an unacceptable level of unsuccessful procedures. These procedures are also tedious and time-consuming, taking several hours to accomplish. Pulmonary vein ostial ablation is proving to be difficult to do, and has led to rapid stenosis and potential occlusion of the pulmonary veins. There is therefore a need for improved atrial ablation products and techniques.

SUMMARY OF THE INVENTION

According to a first aspect of the invention, an ablation system used by an operator to treat a patient is disclosed. The system comprises an ablation catheter that has a flexible shaft with a proximal end and a distal end, and includes at least one ablation element for delivering energy to tissue. The system further comprises an interface unit that provides energy to the ablation catheter. The at least one ablation element is configured to rapidly transition from a first temperature to a second temperature. The first temperature approaches tissue ablation temperature, preferably 60° C., and the second temperature approaches body temperature, typically 37° C. In a preferred embodiment, the at least one ablation element has a majority of surface area in contact with circulating blood when energy is being delivered to the tissue. The majority of this blood exposed surface area is at least 60%, preferably more than 75% and potentially greater than 85% of the total surface area of the electrode. Numerous electrode configurations are described including three segment ("triangle"), semicircular and crescent cross sections, cross sections with curvilinear, serpentine and zigzag segments; cross sections with segments with projecting fins, and cross sections that include an energy delivery portion and a non-energy delivery portion. The electrodes of the present invention are configured to rapidly cool, during energy delivery such as in bipolar energy delivery that follows monopolar energy delivery; and when no energy is being delivered. The electrodes of the present invention are configured to transition from ablation temperature to body temperature in less than 20 seconds, preferably less than 10 seconds. These electrodes are also configured to transition from body temperature to ablation temperature in less than 5 seconds.

According to a second aspect of the invention, an ablation system used by an operator to treat a patient is disclosed. The system comprises an ablation catheter that has a flexible shaft with a proximal end and a distal end, and includes at least one ablation element for delivering energy to tissue. The system further comprises an interface unit that provides energy to the ablation catheter. The at least one ablation element is configured such that a majority of its external surface area is in contact with tissue when energy is delivered to that tissue. The electrode is configured such that at least 60% of the total surface area is in tissue contact, preferably 70% or more. Numerous electrode configurations are described including three segment ("triangle"), semicircular and crescent cross sections, cross sections with curvilinear, serpentine and zigzag segments; cross sections with segments with projecting fins, and cross sections that include an energy delivery portion and a non-energy delivery portion. The electrodes of the present invention are configured to maximize the amount of energy transferred to the tissue, thus minimizing the amount of energy delivered to the blood, such as undesired energy which may cause a blood clot.

According to a third aspect of the invention, an ablation system used by an operator to treat a patient is disclosed. The system comprises a first ablation catheter that has a flexible shaft with a proximal end and a distal end, and includes at least one ablation element for delivering energy to tissue; and a second ablation catheter that has a flexible shaft with a proximal end and a distal end, and includes at least one ablation element for delivering energy to tissue. The system further comprises an interface unit that provides energy to the ablation catheter. The energy delivered by the system is limited by a threshold that is a first value when the first ablation catheter is in use and a different value when the second ablation catheter is in use. The first and second ablation catheters preferably include one or more different functional elements, such as different ablation elements and/or patterns of ablation elements. Ablation elements can be varied in size and cross sectional geometry, cooling and heating properties, type of energy delivered, and other electrode parameters.

According to a fourth aspect of the invention, an ablation system used by an operator to treat a patient is disclosed. The system comprises an ablation catheter that has a flexible shaft with a proximal end and a distal end, and includes at least one ablation element for delivering energy to tissue. The system further comprises an interface unit that provides energy to the ablation catheter. The energy delivered by the interface unit is configured to (1) achieve a target energy level t a target tissue depth; and (2) pulse energy such that the tissue surrounding the electrode does not exceed a threshold temperature. In a preferred embodiment, the energy delivered is RF energy, and the system is configured to automatically transition between bipolar and monopolar RF delivery. Energy delivery is adjusted based on a value selected from the group consisting of: temperature of tissue; rate of change of temperature of tissue; temperature of the at least one ablation element; rate of change of temperature of the at least one ablation element; EKG; tissue thickness; tissue location; cardiac flow rate; and combinations thereof. Automatic adjustments are made to minimize depth of the lesion, minimize the width of the lesion, or both. In a preferred embodiment, the energy delivery is adjusted to achieve a target depth of the lesion. Temperature information is preferably provided by one or more temperature sensors, such as sensors mounted in, on or near an ablation element.

According to a fifth aspect of the invention, an ablation system used by an operator to treat a patient is disclosed. The system comprises an ablation catheter that has a flexible shaft with a proximal end and a distal end, and includes at least one ablation element for delivering energy to tissue. The system further comprises an interface unit that provides energy to the ablation catheter. The interface unit monitors one or more parameters of the system, and prevents the energy delivered from exceeding a threshold. The value of the threshold is determined by the at least one ablation element. The system parameters are preferably selected from the group consisting of: temperature such as temperature from a temperature sensor; a value of measured current; a value of measured voltage; a flow measurement value; a force measurement value such as a measurement of strain; a pressure measurement value; and combinations thereof. The threshold is preferably an energy delivery threshold selected from the group consisting of: peak energy such as peak energy below 10 Watts; average energy such as average energy below 5 Watts; and cumulative energy such as a value below 500 Watt-seconds or less than 300 Watt-seconds; and combinations thereof. In another preferred embodiment, the interface unit includes a threshold comparator for comparing a measured, calculated or otherwise determined value to the threshold. In another preferred embodiment, the threshold changes over time. In yet another preferred embodiment, the system is configured to deliver a low level energy delivery followed by a higher level energy delivery. During or immediately following the low level energy delivery, a threshold value is determined which is utilized in the subsequent higher level energy delivery.

According to a sixth aspect of the invention, an ablation catheter device is disclosed. The ablation catheter comprises an elongated, flexible, tubular body member having a proximal end, a distal end, and a lumen extending therebetween. A control shaft is coaxially disposed and is slidingly received within the lumen of the tubular body member. The catheter further comprises a flexible carrier assembly which includes at least two arms, each arm including at least one ablation element used to deliver energy to tissue. Each ablation element includes a relatively uniform triangle cross-section along its length, with a continuous or discontinuous perimeter or path. The cross section is preferably an isosceles triangle wherein the common base is opposite two sides that determine a vertex angle. This vertex angle is configured, based on the number of carrier arms of the particular carrier assembly, to allow a number of electrodes to be constrained into a volumetrically efficient circle or "pie" shape, the sum of all the vertex angles approximating 360 degrees, such that:

$$\text{Vertex Angle} = \frac{360 \text{ degrees}}{\text{Number of Carrier Arms}}$$

In an alternative embodiment, at least one cross section is dissimilar, and/or the cross sections do not include only isosceles triangle geometries. In these configurations, the relevant (vertex) angles are configured such that their sum approaches 360 degrees in total, similarly providing efficiently constrainable volumes when maintained within the lumen of carrier assembly.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings:

FIG. 2b is a sectional view of a finned electrode of FIG. 2a.

FIG. 4 illustrates a perspective, partial cutaway view of a preferred embodiment of an ablation catheter consistent with the present invention in which the carrier element has three carrier arms each including two ablation elements.

FIG. 4a is a sectional view of a distal portion of the ablation catheter of FIG. 4.

DESCRIPTION OF THE EMBODIMENTS

Figure 1:
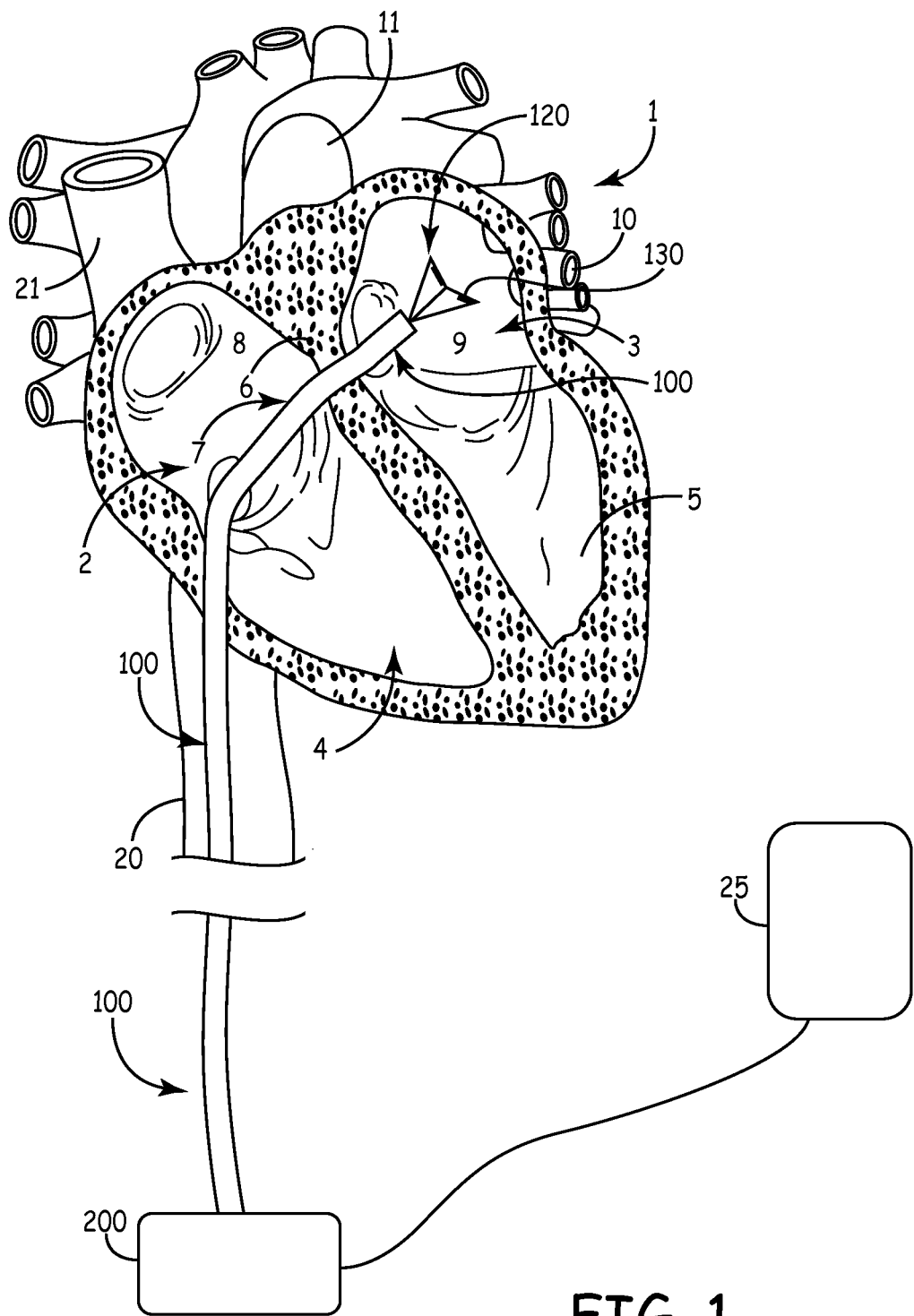
FIG. 1 illustrates the treatment to be accomplished with the devices and methods described below.

Reference will now be made in detail to the present embodiments of the invention, examples of which are illustrated in the accompanying drawings. Wherever possible, the same reference numbers will be used throughout the drawings to refer to the same or like parts.

The present invention utilizes ablation therapy. Tissue ablation is often used in treating several medical conditions, including abnormal heart rhythms. Ablation can be performed both surgically and non-surgically. Non-surgical ablation is typically performed in a special lab called the electrophysiology (EP) laboratory. During this non-surgical procedure a catheter is inserted into a vessel such as a vein, and guided into the heart using fluoroscopy for visualization. Subsequently, an energy delivery apparatus is used to supply energy to the heart muscle. This energy either "disconnects" or "isolates" the pathway of the abnormal rhythm. It can also be used to disconnect the conductive pathway between the upper chambers (atria) and the lower chambers (ventricles) of the heart. For individuals requiring heart surgery, ablation can be performed during coronary artery bypass or valve surgery.

The present invention provides catheters for performing targeted tissue ablation in a subject. In preferred embodiments, the catheters comprise a tubular body member having a proximal end and distal end and preferably a lumen extending therebetween. The catheter is preferably of the type used for performing intracardiac procedures, typically being introduced from the femoral vein in a patient's leg or a vein in the patient's neck. The catheter is preferably introducible through a sheath with a steerable tip that allows positioning of the distal portion to be used, for example, when the distal end of the catheter is within a heart chamber. The catheters include ablation elements mounted on a carrier assembly. The carrier assembly is preferably attached to a coupler, which in turn is connected to a control shaft that is coaxially disposed and slidingly received within the lumen of the tubular body member. The carrier assembly is deployable from the distal end of the tubular body member by advancing the control shaft, such as to engage one or more ablation elements against cardiac tissue, which is typically atrial wall tissue or other endocardial tissue. Retraction of the control shaft causes the carrier assembly to be constrained within the lumen of the tubular body member.

Arrays of ablation elements, preferably electrode arrays, may be configured in a wide variety of ways and patterns. In particular, the present invention provides devices with electrode arrays that provide electrical energy, such as radiofrequency (RF) energy, in monopolar (unipolar), bipolar or combined monopolar-bipolar fashion, as well as methods for treating conditions (e.g., atrial fibrillation, supra ventricular tachycardia, atrial tachycardia, ventricular tachycardia, ventricular fibrillation, and the like) with these devices. Alternative to or in combination with ablation elements that deliver electrical energy to tissue, other forms and types of energy can be delivered including but not limited to: sound energy such as acoustic energy and ultrasound energy; electromagnetic energy such as electrical, magnetic, microwave and radiofrequency energies; thermal energy such as heat and cryogenic energies; chemical energy such as energy generated by delivery of a drug; light energy such as infrared and visible light energies; mechanical and physical energy; radiation; and combinations thereof.

As described above, the normal functioning of the heart relies on proper electrical impulse generation and transmission. In certain heart diseases (e.g., atrial fibrillation) proper electrical generation and transmission are disrupted or are otherwise abnormal. In order to prevent improper impulse generation and transmission from causing an undesired condition, the ablation catheters of the present invention may be employed.

One current method of treating cardiac arrhythmias is with catheter ablation therapy, which, to date, has been difficult and impractical to employ. In catheter ablation therapy, physicians make use of catheters to gain access into interior regions of the body. Catheters with attached electrode arrays or other ablating devices are used to create lesions that disrupt electrical pathways in cardiac tissue. In the treatment of cardiac arrhythmias, a specific area of cardiac tissue having aberrant conductive pathways, such as atrial rotors, emitting or conducting erratic electrical impulses, is initially localized. A user (e.g., a physician such as an electrophysiologist) directs a catheter through a main vein or artery into the interior region of the heart that is to be treated. The ablating element is next placed near the targeted cardiac tissue that is to be ablated. The physician directs energy, provided by a source external to the patient, from one or more ablation elements to ablate the neighboring tissue and form a lesion. In general, the goal of catheter ablation therapy is to disrupt the electrical pathways in cardiac tissue to stop the emission of and/or prevent the propagation of erratic electric impulses, thereby curing the heart of the disorder. For treatment of atrial fibrillation, currently available methods and devices have shown only limited success and/or employ devices that are extremely difficult to use or otherwise impractical.

The ablation catheters of the present invention allow the generation of lesions of appropriate size and shape to treat conditions involving disorganized electrical conduction (e.g., atrial fibrillation). The ablation catheters of the present invention are also practical in terms of ease-of-use and limiting risk to the patient, as well as significantly reducing procedure times. The present invention accomplishes these goals by, for example, the use of spiral shaped and radial arm shaped (also called umbrella shaped) carrier assemblies whose ablation elements create spiral, radial, or other simple or complex shaped patterns of lesions in the endocardial surface of the atria by delivery of energy to tissue or other means. The lesions created by the ablation catheters are suitable for inhibiting the propagation of inappropriate electrical impulses in the heart for prevention of reentrant arrhythmias.

Definitions. To facilitate an understanding of the invention, a number of terms are defined below.

As used herein, the terms "subject" and "patient" refer to any animal, such as a mammal like livestock, pets, and preferably a human. Specific examples of "subjects" and "patients" include, but are not limited to, individuals requiring medical assistance, and in particular, requiring atrial fibrillation catheter ablation treatment.

As used herein, the terms "catheter ablation" or "ablation procedures" or "ablation therapy," and like terms, refer to what is generally known as tissue destruction procedures.

As used herein, the term "ablation element" refers to an energy delivery element, such as an electrode for delivering electrical energy. Ablation elements can be configured to deliver multiple types of energy, such as ultrasound energy and cryogenic energy, either simultaneously or serially. Electrodes can be constructed of a conductive plate, wire coil, or other means of conducting electrical energy through contacting tissue. In monopolar energy delivery, the energy is conducted from the electrode, through the tissue to a ground pad, such as a conductive pad attached to the back of the patient. The high concentration of energy at the electrode site causes localized tissue ablation. In bipolar energy delivery, the energy is conducted from a first electrode to one or more separate electrodes, relatively local to the first electrode, through the tissue between the associated electrodes. Bipolar energy delivery results in more precise, shallow lesions while monopolar delivery results in deeper lesions. Both monopolar and bipolar delivery provide advantages, and the combination of their use is a preferred embodiment of this application. Energy can also be delivered using pulse width modulated drive signals, well known to those of skill in the art. Energy can also be delivered in a closed loop fashion, such as a system with temperature feedback wherein the temperature modifies the type, frequency and or magnitude of the energy delivered.

As used herein, the term "carrier assembly" refers to a flexible carrier, on which one or more ablation elements are disposed. Carrier assemblies are not limited to any particular size, or shape, and can be configured to be constrained within an appropriately sized lumen.

As used herein, the term "spiral tip" refers to a carrier assembly configured in its fully expanded state into the shape of a spiral. The spiral tip is not limited in the number of spirals it may contain. Examples include, but are not limited to, a wire tip body with one spiral, two spirals, ten spirals, and a half of a spiral. The spirals can lie in a relatively single plane, or in multiple planes. A spiral tip may be configured for energy delivery during an ablation procedure.

As used herein the term "umbrella tip" refers to a carrier assembly with a geometric center which lies at a point along the axis of the distal portion of the tubular body member, with one or more bendable or hinged carrier arms extending from the geometric center, in an umbrella configuration. Each carrier arm may include one or more ablation elements. Each carrier arm of an umbrella tip includes a proximal arm segment and a distal arm segment, the distal arm segment more distal than the proximal arm segment when the carrier assembly is in a fully expanded condition. One or more additional carrier arms can be included which include no ablation elements, such as carrier arms used to provide support or cause a particular deflection. An umbrella tip body is not limited to any particular size. An umbrella tip may be configured for energy delivery during an ablation procedure.

As used herein, the term "lesion," or "ablation lesion," and like terms, refers to tissue that has received ablation therapy. Examples include, but are not limited to, scars, scabs, dead tissue, burned tissue and tissue with conductive pathways that have been made highly resistive or disconnected.

As used herein, the term "spiral lesion" refers to an ablation lesion delivered through a spiral tip ablation catheter. Examples include, but are not limited to, lesions in the shape of a wide spiral, and a narrow spiral, a continuous spiral and a discontinuous spiral.

As used herein, the term "umbrella lesion" or "radial lesion," and like terms, refers to an ablation lesion delivered through an umbrella tip ablation catheter. Examples include, but are not limited to, lesions with five equilateral prongs extending from center point, lesions with four equilateral prongs extending from center point, lesions with three equilateral prongs extending from center point, and lesions with three to five non-equilateral prongs extending from center point.

As used herein, the term "coupler" refers to an element that connects the carrier assembly to the control shaft. Multiple shafts, or ends of the carrier assembly may connect to the coupler. Multiple carrier arms can have one or more of their ends attached to the coupler. The coupler may include anti-rotation means that work in combination with mating means in the tubular body member. Couplers may be constructed of one or more materials such as polyurethane, steel, titanium, and polyethylene.

As used herein, the term "carrier arm" refers to a wire-like shaft capable of interfacing with electrodes and the coupler. A carrier arm is not limited to any size or measurement. Examples include, but are not limited to: stainless steel shafts; Nitinol shafts; titanium shafts; polyurethane shafts; nylon shafts; and steel shafts. Carrier arms can be entirely flexible, or may include flexible and rigid segments.

As used herein, the term "carrier arm bend point" refers to a joint (e.g., junction, flexion point) located on a carrier arm. The degree of flexion for a carrier arm bend point may range from 0 to 360 degrees. The bend portion can be manufactured such that when the carrier assembly is fully expanded, the bend point is positioned in a relatively straight configuration, a curved configuration, or in a discrete transition from a first direction to a second direction, such as a 45 degree bend transition. The bend portion can include one or more flexing means such as a spring, a reduced diameter segment, or a segment of increased flexibility.

The present invention provides structures that embody aspects of the ablation catheter. The present invention also provides tissue ablation systems and methods for using such ablation systems. The illustrated and various embodiments of the present invention present these structures and techniques in the context of catheter-based cardiac ablation. These structures, systems, and techniques are well suited for use in the field of cardiac ablation.

However, it should be appreciated that the present invention is also applicable for use in other tissue ablation applications such as tumor ablation procedures. For example, the various aspects of the invention have application in procedures for ablating tissue in the prostrate, brain, gall bladder, uterus, and other regions of the body, preferably regions with an accessible wall or flat tissue surface, using systems that are not necessarily catheter-based.

The multifunctional catheters of the present invention have numerous advantages over previous prior art devices. The present invention achieves efficiency in tissue ablation by maximizing contact between electrodes and tissue, such as the atrial walls, while also achieving rapid and/or efficient transfer of heat from the electrode into the circulating blood ("cooling"), such as by maximizing electrode surface area in contact with circulating blood. To achieve this result, in a preferred embodiment the electrode has a projecting fin that is configured to act as a heat sink that provides rapid and efficient cooling of the electrode. In another preferred embodiment the electrode comprises two components such that one component, the electrode conductive portion, contracts tissue and the other component, the nonconductive portion, remains thermally conductive. The present invention includes electrodes with improved and miniaturized cross sectional geometries and carrier assemblies that "fold-up" efficiently to allow a smaller ablation catheter to be employed. These improved electrodes are preferably triangularly shaped as described in detail in reference to subsequent figures below. Because these triangular electrodes fold up efficiently, and can have either a "base" to contact tissue or a "point" to contact tissue, greater efficiency and versatility are achieved. The devices and systems are configured to minimize the amount of tissue ablated while still achieving the desired therapeutic benefit of the ablation therapy. Ablated lesions are created with a target depth, and minimal widths. System components monitor energy delivered, parameters associated with energy delivered and other system parameters. Energy delivered is prevented from achieving one or more threshold values.

FIGS. 1-12 show various embodiments of the multifunctional catheters of the present invention. The present invention is not limited to these particular configurations.

FIG. 1 illustrates the treatment to be accomplished with the devices and methods described hereinbelow. FIG. 1 shows a cutaway view of the human heart 1 showing the major structures of the heart including the right atrium 2, the left atrium 3, the right ventricle 4, and the left ventricle 5. The atrial septum 6 separates the left and right atria. The fossa ovalis 7 is a small depression in the atrial septum that may be used as an access pathway to the left atrium from the right atrium. The fossa ovalis 7 can be punctured, and easily reseals and heals after procedure completion. In a patient suffering from atrial fibrillation, aberrant electrically conducive tissue may be found in the atrial walls 8 and 9, as well as in the pulmonary veins 10 and the pulmonary arteries 11. Ablation of these areas, referred to arrhythmogenic foci (also referred to as drivers or rotors), is an effective treatment for atrial fibrillation. Though circumferential ablation of the pulmonary vein usually cures the arrhythmia that originates in the pulmonary veins, as a sole therapy it is usually associated with lesions that have high risk of the eventual stenosis of these pulmonary veins, a very undesirable condition. The catheters of the present invention provide means of creating lesions remote from these pulmonary veins and their ostia while easily being deployed to ablate the driver and rotor tissue.

To accomplish this, catheter 100 is inserted into the right atrium 2, preferably through the inferior vena cava 20, as shown in the illustration, or through the superior vena cava 21. Catheter 100 may include an integral sheath, such as a tip deflecting sheath, or may work in combination with a separate sheath. When passing into the left atrium, the catheter passes through or penetrates the fossa ovalis 7, such as over a guide wire placed by a trans-septal puncture device. The catheter 100 carries a structure carrying multiple ablation elements such as RF electrodes, carrier assembly 120, into the left atrium. Carrier assembly 120, which includes multiple electrodes 130, can be advanced and retracted out of distal end of catheter 100. Carrier assembly 120 is adapted to be deformable such that pressing carrier assembly 120 into left atrial wall 9 will cause one or more, and preferably all of electrodes 130 to make contact with tissue to be analyzed and/or ablated. Each of the electrodes 130 is attached via connecting wires to an energy delivery apparatus, RF delivery unit 200, which is also attached to patch electrode 25, preferably a conductive pad attached to the back of the patient.

RF delivery unit 200 is configured to deliver RF energy in monopolar, bipolar or combination monopolar-bipolar energy delivery modes. In a preferred embodiment, monopolar energy delivery is followed by bipolar energy delivery. In an alternative embodiment, the bipolar energy is then followed by a period without energy delivery; such as a sequence in which the three steps are have equal durations. In another preferred embodiment, RF delivery unit 200 is configured to also provide electrical mapping of the tissue that is contacted by one or more electrodes integral to carrier assembly 120. Electrodes 130, preferably with a triangular cross section, can also be configured to be mapping electrodes and/or additional electrodes can be integral to carrier assembly 120 to provide a mapping function. Carrier assembly 120 is configured to be engaged over an endocardial surface to map and/or ablate tissue on the surface. RF energy is delivered after a proper location of the electrodes 130 is confirmed with a mapping procedure. If the position is determined to be inadequate, carrier assembly 120 is repositioned through various manipulations at the proximal end of the ablation catheter 100. In another preferred embodiment, RF delivery unit 200 is configured to deliver both RF energy and ultrasound energy through identical or different electrodes 130. In another preferred embodiment, RF delivery unit 200 is configured to accept a signal from one or more sensors integral to ablation catheter 100, not shown, such that the energy delivered can be modified via an algorithm which processes the information received from the one or more sensors. The improved electrodes and other catheter and system components of the present invention typically require only 3 to 5 watts of RF energy to adequately ablate the tissue. The minimal power requirements results in reduced procedure time as well as greatly enhanced safety of the overall procedure.

Figure 2A:
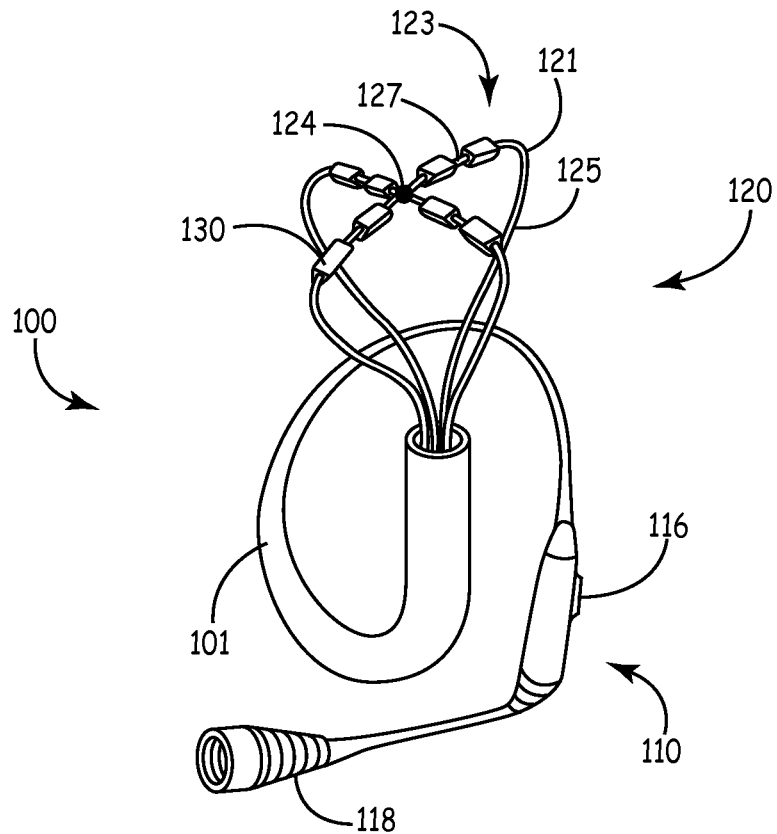
FIG. 2a illustrates a perspective view of an ablation catheter consistent with the present invention in which the carrier element has four carrier arms, each including two ablation elements.
Figure 2B:
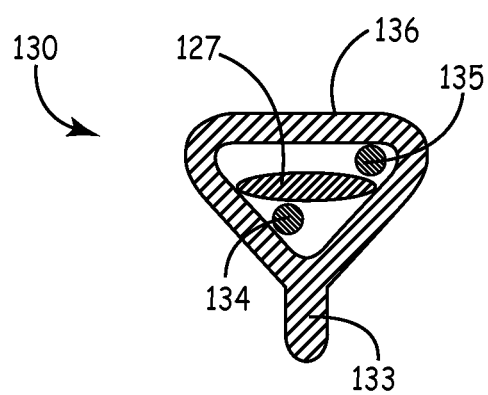

FIGS. 2a and 2b illustrate an exemplary embodiment of the ablation catheter 100 of the present invention. These ablation catheters have triangular electrodes 130, each with fin 133 configured to provide rapid and efficient cooling of electrode 130. The cooling efficiency prevents over-heating of the electrode and neighboring tissue during ablation, as well as a short transition time from an ablation temperature, preferably 60° C., to body temperature, typically 37° C. after an ablation cycle has ceased. This rapid transition is typically less than 20 seconds, even when the electrode remains in contact with recently ablated tissue. Other benefits of the rapid and efficient cooling electrode configuration include reducing the risk of blood clotting.

The ablation elements of the present invention include RF energy delivery electrodes 130 of FIGS. 2a and 2b, as well as other elements capable of delivering one or more forms of energy, described in detail hereinabove, the electrodes and other system components configured in a manner sufficient to controllably ablate tissue. Electrodes 130 include conductive materials, such as a metal or metal-coated material. Metals and combinations of metals are appropriate such as: platinum, iridium, gold, stainless steel and aluminum. Conductive polymers are also appropriate materials. Conductive surfaces may be painted, coated or plated surfaces, such as gold plated over a copper base. Electrode materials may also include foils such as aluminum or gold foils attached to a base. Electrodes 130 deliver RF energy in monopolar or bipolar mode as has been described in reference to FIG. 1. Electrodes 130 are designed to have small surface area, typically less than 2.5 mm$^2$ and preferably approximating 0.56 mm$^2$. Electrodes 130 are designed to have small volume, typically less than 3.0 mm$^3$ and preferably approximating 1.3 mm$^3$. Electrodes 130 are designed to have small mass, typically less than 0.05 grams, and preferably approximating 0.03 grams. These miniaturized electrodes, especially those with a triangular cross section, provide numerous advantages such as high ratio of energy to surface area (energy density) during ablation, as well as efficiently compact volume of carrier assembly 120 when constrained within the lumen of the ablation catheter in the retracted, undeployed state.

FIG. 2a shows the structures of the ablation carrier assembly 120 and other portions of ablation catheter 100. The ablation carrier assembly 120 shown includes carrier arms 123 that extend radially out from the central axis of the distal end of catheter shaft 101, the carrier arms 123 positioned in a symmetric configuration with equal angles (ninety degrees in a four arm configuration between each arm). Carrier assembly 120 is shown with four carrier arms 123, however any number can be used, and each arm can carry one or more mapping or ablating electrodes 130, or be void of electrodes. Carrier arms 123 are resiliently biased, preferably constructed of a wire such as a ribbon wire, and may have segments with different levels of flexibility. Carrier arms 123 are shown with multiple electrodes 130 fixedly mounted (such as with glues, soldering, welding, crimping or other attachment means) to its distal arm segment 127. In an alternative embodiment, different patterns of electrodes are employed, and one or more arms may be void of electrodes such as where carrier arm 123 provides support only. In a preferred embodiment, different types of ablation elements are mounted to one or more carrier arms 123, such as electrodes with different geometries, or ablation elements that deliver different forms of energy. Carrier arms 123 may also include mapping electrodes, thermal sensors or other sensors, with or without the inclusion of ablation elements. In a preferred embodiment, each carrier arm 123 includes at least one ablation element. In alternative embodiments, three or more arms can be separated by non-equal angles.

Each carrier arm 123 includes proximal arm segment 125 and distal arm segment 127. Electrodes 130 are mounted onto distal arm segment 127. During the ablation procedure, an operator presses distal arm segment 127 into tissue prior to and during energy delivery. Carrier assembly 120 is configured with specific rigidity such that the operator can exert a nominal force to cause the appropriate electrodes 130 to press and slightly "bury" into the tissue, without perforating or otherwise damaging the neighboring tissue. In a preferred embodiment, the distal arm segments contain thermocouples such as sensors embedded in the electrodes 130, or sensors mounted equidistant between two electrodes 130. Proximal arm segment 125 and distal arm segment 127 connect at a bendable joint, carrier arm bend point 121. In a preferred embodiment, proximal arm segment 125, distal arm segment 127 and bend point 121 are a continuous resiliently flexible wire. Each distal arm segment 127 bends radially inward from the bend point 121 toward the longitudinal axis of catheter shaft 101. The distal arm segments 127 are shown also to tend proximally, to establish an acute angle with the proximal arm segment 125 from which it extends, and the angle is small such that the distal end of the distal arm segment 127 is proximal to the carrier arm bend point 121. Bend point 121 allows "folding out" of carrier assembly 120 during retraction, acting as a hinge in providing the means for rotatably joining the distal arm segment 127 to the proximal arm segment 125. The proximal arm segment 125 of the carrier arm 123 may include temperature sensors, not shown, such as thermocouples to measure temperature of blood. In the configuration shown, the proximal arm segment 125 will not contact tissue during the ablation procedure. In an alternative embodiment, proximal arm segment 125 includes one or more electrodes, for ablation and/or for mapping, such that the opposite side of carrier assembly 120 can be used to map or ablate tissue and is configured to contact tissue, such as when carrier assembly 120 is deployed and catheter shaft 101 is in tension such as when pulled back by an operator.

Each distal arm segment 127 connects, at its end opposite bend point 121, to connection point 124, a mechanical joint such as a soldered, crimped or welded connection that stabilizes each distal arm segment 127 relative to the others. In a preferred embodiment, two continuous wires or ribbons are used to create the four distal arm segments 127. Each wire or ribbon comprises the pair of distal arm segments 127 that are linearly aligned, and the two wires are connected at their midpoint at connection point 124. These wires or ribbons are preferably constructed of Nitinol, but other materials such as stainless steel or a plastic may be used. In an alternative embodiment, the two connection wires are resiliently biased to deploy in the configuration shown in FIG. 2a, but do not include connection point 124 such that the center portion of the two continuous wires can move relative to each other.

Referring to the ablation catheter 100 structures, FIG. 2a shows a tubular body member that is an elongated, flexible, hollow tube, catheter shaft 101, which connects at its proximal end to handle 110. The material used for the construction of the catheter shaft 101 and each component which resides or is configured to be inserted through a lumen integral to catheter shaft 101, are selected to provide the suitable flexibility, column strength and steerability to allow percutaneous introduction of ablation catheter 100 through the vasculature of the patient, entering the right atrium 2 through the septum 6 and into the left atrium 3. Catheter shaft 101 and other tubular conduits of ablation catheter 100 are constructed of materials such as Pebax, urethanes, nylons, thermoplastic elastomers, and polyimides. The shafts may be reinforced with wire or plastic braids and/or may include coil springs. Catheter shaft 101 is typically between 4 to 12 French and typically 6 to 8 French. In a preferred embodiment, catheter shaft 101 is introduced through a deflectable sheath where the sheath mechanism is already in place in left atrium 3. In an alternative embodiment, catheter 100 is inserted directly without the use of an outer sheath, and catheter 100 includes a deflectable tip assembly and deflection controls.

Handle 110 on the ablation catheter includes controls to operate the carrier assembly 120. Handle 110 is constructed of a rigid or semi-rigid material such as Delrin or polycarbonate, and includes button 116 that is connected to switch means, not shown, for starting and/or stopping the delivery of energy to one or more of electrodes 130. Handle 110 may include other controls, not shown, to perform numerous functions such as change energy delivery settings. Handle 110 may include a retraction mechanism, not shown, to advance and retreat carrier assembly 120. In an alternative embodiment, handle 110 is attached to an inner shaft slidingly received within catheter shaft 101 such that retraction of the handle 110 causes the carrier assembly 120 to collapse and be constrained within the lumen at end of catheter shaft 101. Carrier arm 123 is resiliently biased in shown position so that it can be collapsed and withdrawn within lumen of catheter shaft 101 through manipulation of handle 110 on proximal end of catheter 100.

Handle 110 includes a plug 118 that attaches to an interface unit of the present invention, such as an RF energy generator that also includes mapping functions and display. Plug 118 is connected to electrical wires that extend distally with a lumen integral to catheter shaft 101 of carrier assembly 120, terminating at each of the electrodes 130.

FIG. 2b illustrates the cross section, preferably a uniform cross section, of one or more electrodes 130 mounted to distal arm segment 127 of FIG. 2a. A projecting member, fin 133, assists in the rapid and efficient cooling of electrode 130 during and after ablation energy application, acting as a heat sink and efficiently transferring heat energy to the neighboring blood, such as blood circulating in the left atrium 3 or the right atrium 2 depending upon where the carrier assembly 120 has been placed by the operator. The size, surface area and mass of fin 133 are chosen to effectively transfer the heat energy while allowing carrier assembly 120 to achieve a sufficiently compact configuration when constrained within the lumen of the ablation catheter. In a preferred embodiment, fin 133 is sized such that the portion of the surface area of electrode 130 that is in contact with circulating blood is at least 60%, and preferably 70% of the total surface area of electrode 130. Fin 133 may change laminar and/or other non-turbulent flows to turbulent flow, such that heat is more efficiently transmitted away from electrode 130. In an alternative embodiment, illustrated and described in reference to FIGS. 5c and 5d, fin 133 may be electrically isolated from the remainder of electrode 130, such that fin 133 does not deliver energy to the circulating blood. In another alternative embodiment, illustrated and described in reference to FIG. 6b, electrode 130 may include multiple fins.

First wire 134 is an energy delivery conduit that connects to electrode 130 to transfer ablation energy and preferably to also send and/or receive signals to map the tissue of the heart. Second wire 135 depicts an exemplary wire that connects to electrode 130, and may act as the return wire to first wire 134, for return of ablation energy and/or mapping signals. Wire 134 and wire 135 are typically 30 awg wire including a 0.003" polyamide insulating outer jacket, each parameter chosen to carry sufficient ablation currents and prevent voltage breakdown between neighboring wires. The efficiency of the electrodes of the present invention, as well as the efficient configuration of the other components of the system, allow greatly reduced wire gauge and insulation thickness, correlating to smaller diameter and more flexible ablation catheters.

Surface 136 is the base of the electrode that is the part of the structure that contacts tissue during ablation. In a preferred embodiment, surface 136 is a small surface area so that energy delivered per square area is maximized. Fin 133 projects from the apex opposite surface 136, and provides sufficient surface area such that the majority of the surface area of electrode 130 resides in the circulating blood when surface 136 is in contact with tissue and energy is being delivered. Within the triangular cross section of electrode 130 passes each wire 134 and 135, as well as distal arm segment 127, to which electrode 130 is fixedly mounted.

Figure 3A:
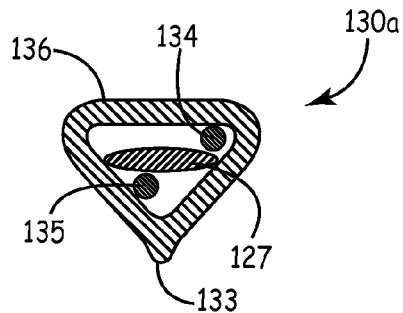
FIG. 3a is a sectional view of an ablation element consistent with the present invention.
Figure 3B:
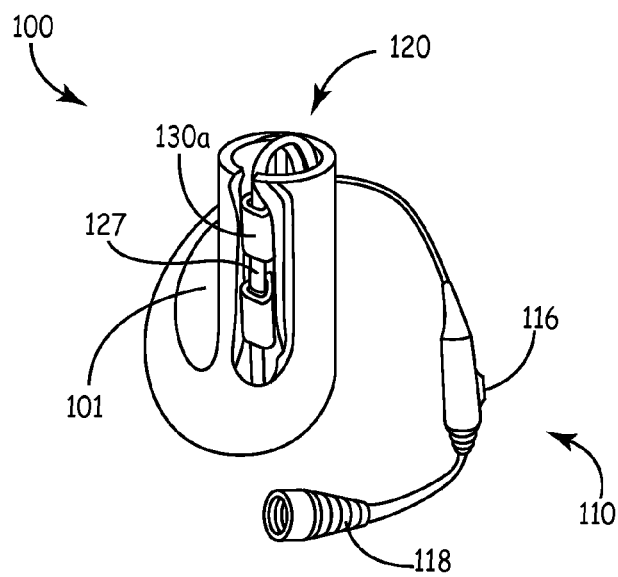
FIG. 3b is a sectional view of multiple ablation elements of FIG. 3a shown constrained in the distal end of an ablation catheter of the present invention.
Figure 3C:
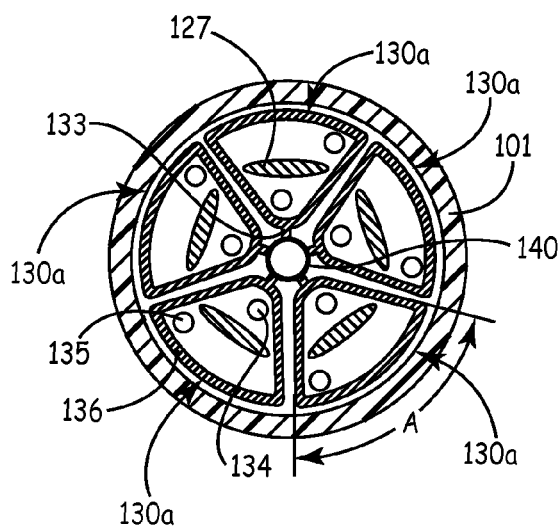
FIG. 3c is a perspective, partial cutaway view of the ablation catheter of FIG. 3b.

Referring now to FIGS. 3a through 3c, another preferred embodiment of the ablation catheter and components of the ablation system of the present invention is illustrated. Electrodes 130 have a triangular cross section with a continuous perimeter or path, preferably an isosceles triangle wherein the common base is opposite two sides that determine a vertex angle. This vertex angle is configured, based on the number of carrier arms of the particular carrier assembly, to allow a number of electrodes to be constrained into a volumetrically efficient circle or "pie" shape, the sum of all the vertex angles approximating 360 degrees, such that:

$$\text{Vertex Angle} = \frac{360 \text{ degrees}}{\text{Number of Carrier Arms}}$$

In an alternative embodiment, the cross sections are dissimilar, and/or the cross sections do not include only isosceles geometries, however the individual vertex angles are configured such that their sum approaches 360 degrees in total, providing efficient constrained volume of the carrier assembly. In addition to allowing compact constrained volume, and overall small surface area, volume and mass of electrodes 130, the electrodes of the present invention provide maximum flexibility in performing ablation procedures, such as by: minimizing energy delivered to blood; avoiding energy delivered to non-targeted tissue and/or minimizing tissue area receiving energy during ablation; maximizing energy density delivered to tissue; reducing procedure time, and other advantages. In a preferred embodiment, the ablation catheter and system of the present invention includes multiple dissimilar electrodes, fixedly mounted to a single ablation catheter or mounted to multiple ablation catheters used sequentially or simultaneously in a single ablation procedure for a patient.

Referring specifically to FIG. 3a, electrode 130a is configured to deliver RF energy to tissue via surface 136. Electrode 130a of FIG. 3a is similar to electrode 130 of FIG. 2b with a smaller projecting fin 133, sized to allow a more compact constrained configuration of the carrier assembly while still increasing the surface area of electrode 130a in the circulating blood during ablation. Electrode 130a is fixedly mounted to distal arm segment 127 which comprises a Nitinol wire or ribbon but alternatively a non-conductive material such as nylon or other non-metal which does not require electrode 130a from being electrically isolated from distal arm segment 27, isolation means not shown. Electrode 130a includes within its triangular cross section wire 134 and wire 135 that are electrically connected to electrode 140a and travel proximally to an electrical connection point that attaches to an interface unit of the present invention. Wire 134 and 135 provide supply and return of RF power and potentially supply and return of mapping drive and record signals. Additional wires and other energy delivery or other conduits, not shown, may pass through the triangular cross section of electrode 130a, such as energy and/or signal delivery conduits that connect to sensors such as thermocouples, or other ablation or mapping elements. In a preferred embodiment, electrode 130a includes an embedded thermocouple, not shown but preferably a bimetallic thermocouple consisting of copper and alloy 11 or Constantan alloy. Each thermocouple is attached to 40 awg wire with a 0.001" insulating jacket, the wires traveling proximally and attaching to the interface unit of the present invention for converting signals to temperature values.

Referring to FIG. 3b, a partial cutaway view of the ablation catheter of the present invention is illustrated, including the multiple electrodes 130a of FIG. 3a constrained with a lumen of catheter shaft 101 of ablation catheter 100. Ablation catheter 100 may be configured to be inserted through a deflectable guide catheter, or include distal tip deflection means, not shown. Electrodes 130a are fixedly mounted to distal arm segments 127 which are attached to proximal arm segments via a bendable portion (both proximal arm segments and bendable portion not shown but described in detail in reference to FIG. 2a). The ablation element carrier assembly has been folded into the retracted state shown, by retraction of handle 110 and/or activation of a control of handle 110, not shown but preferably a sliding knob or lever on handle 110. Handle 110 includes connector 118 for electrical attachment to an energy delivery apparatus such as an RF generator and/or electrophysiology mapping unit, and further includes button 116 used by the operator to initiate an energy delivery event. Handle 110 may additionally include other functional components and assemblies such as other control or activation means, as well as audio and/or tactile transducers to alert the operator of alert conditions.

Referring additionally to FIG. 3c, the carrier assembly of FIGS. 3b and 3c includes five electrodes 130a and five distal arm segments 127 that have been placed in a constrained condition within a lumen of catheter shaft 101 such that at least a portion of each of the triangle cross section of the five electrodes 130a lie in a single plane. Each electrode 130a has a similar isosceles triangle shaped cross section such that the vertex angle A approximates 75 degrees allowing the compact 360 circular or pie shaped configuration. In the constrained configuration shown, each vertex angle A is aligned radially outward from the central axis of shaft 101 such that the tissue contacting surface 136 of each electrode 130a is in relative contact with the inner wall of shaft 101. These triangle cross sections and relatively small projecting fins 133 are sized and configured to allow a compact constrained configuration that includes coupler 140 at its center. Coupler 140, described in detail in reference to FIG. 4, couples the carrier arms of the carrier assembly to a slidable shaft, not shown but operably attached to handle 110 and advanced and retracted by an operator to position the carrier assembly in its deployed (expanded) and constrained configurations respectively.

While the carrier assembly configuration of FIGS. 3b and 3c illustrate a five carrier arm configuration that correlates to an electrode 130a cross section triangular vertex angle approximating 75 degrees, it can be easily derived from the equation above that a vertex angle of 120 degrees would correspond to three arm carrier assembly configurations and a vertex angle of 90 degrees would correspond to four arm configurations. It also should be easily understood that in embodiments in which electrode 130a cross sections are dissimilar, the sum of the vertex angles of the appropriate cross sections, those cross sections that are linearly aligned within the lumen of catheter shaft 101 in the retracted position, should approximate 360 degrees to minimize the overall constrained cross sectional area.

Referring now to FIGS. 4 and 4a, another preferred embodiment of ablation catheter 100 and ablation system of the present invention is illustrated. Catheter 100 includes carrier assembly 120 configured in another umbrella tip configuration. Carrier assembly 120 includes three carrier arms 123, each separated by 120 degrees from the neighboring arm when in the deployed condition, and each of which includes two ablation elements, electrodes 130. In an alternative embodiment, different patterns of electrodes are employed, and one or more arms may be void of electrodes. Electrodes can take on one or more various forms, such as those described in detail in reference to FIGS. 5a through 5f and FIGS. 6a through 6c. The six electrodes 130 shown may have similar or dissimilar characteristics. They may be chosen to maximize cooling or maximize energy delivery to tissue. Each electrode 130 may be energized with one or more forms of energy such as RF energy in a sequence of monopolar and bipolar energy delivery. Referring back to FIG. 4, carrier arms 123 extend radially out from the central axis of the distal end of catheter shaft 101. Each carrier arm 123 includes proximal arm segment 125 and distal arm segment 127, these segments connected at a bendable joint, bend point 121. In a preferred embodiment, proximal arm segment 125 and distal arm segment 127 and bend point 121 are a continuous resiliently flexible wire, such as a "trained" Nitinol wire that creates the umbrella tip. Each electrode 130 is mounted to an insulator, insulating band 131 such that the electrode is electrically isolated from the wire segments of carrier assembly 120. Each electrode 130 is connected to wires that extend along shafts of carrier assembly 120, toward a lumen of catheter shaft 101, and proximally to handle 110. These wires, not shown but described in detail hereinabove, include insulation to electrically isolate one wire from another. One end of each distal arm segment 127 is attached to a cylinder, coupler 140, which is sized to be slidably received within a lumen of catheter shaft 101.

Coupler 140 can be flexible or rigid, and may contain both rigid and flexible portions along its length. Coupler 140 may provide electrical connection means to connect wires extending from the handle to wires from carrier assembly 120 electrodes. The ends of the distal arm segments 127 and the ends of the proximal arm segments 125 can be attached to the outside of coupler 140, the inside of coupler 140 or both. Coupler 140 includes along its outer surface, a projection, projection 142, which has a cross section profile which mates with a recess, groove 106 of catheter shaft 101 which prevents undesired rotation of carrier assembly 120. In an alternative embodiment, catheter shaft 101 includes a projection, and coupler 140 includes a groove to accomplish a similar prevention of rotation. In another alternative embodiment, control shaft 150, which is slidingly received within a lumen of shaft 101, additionally or alternatively includes a projection or other means to mate with shaft 101 to prevent undesired rotation of carrier assembly 120. As depicted in FIG. 4a, control shaft 140 includes a thru lumen, lumen 152, such that ablation catheter 101 can be inserted over a guidewire (guidewire exit on handle 110 not shown). Additionally or alternatively, lumen 152 may include one or more wires or other filamentous conduits extending from proximal handle 110 a point more distal.

Control shaft 150 is mechanically attached to coupler 140. Control shaft 150 extends proximally to handle 110 and is operably connected to knob 115 such that rotation of knob 115 from a deployed position to a withdrawn position causes carrier assembly 120 to be constrained within a lumen of catheter shaft 101, and rotation of knob 115 from a withdrawn position to a deployed position causes carrier assembly 120 to extend beyond the distal end of catheter shaft 101 to be in an expanded condition. In a preferred embodiment, knob 115 is operably connected to control shaft 150 via a cam, or set of gears, not shown, to provide a mechanical advantage in the distance traveled by control shaft 150.

Catheter shaft 101 is preferably part of a steerable sheath, steering mechanism not shown, and includes flush port 170, which is configured to be attachable to a flushing syringe, used to flush blood and other debris or contaminants from the lumen of an empty catheter shaft 101 (wherein control shaft 150, coupler 140 and carrier assembly 120 have been removed) or for flushing the space between control shaft 150 and the inner wall of catheter shaft 101. Catheter shaft 101 is not connected to handle 110, such that handle 110 can be withdrawn, removing control shaft 150, coupler 140 and carrier assembly 120 from catheter shaft 101. This configuration is useful when these components are provided in a kit form, including combinations of different versions of these components, the different combinations made available to treat multiple patients, or a single patient requiring multiple electrode patterns or other varied electrode properties such as tissue contact surface area, electrode cooling properties and temperature sensor location. A preferred example of a kit would include the catheter shaft 101 and flush port 170 of FIG. 6 acting as a sheath; kitted with the insertable shaft assembly comprising handle 110, control shaft 150, coupler 140 and umbrella tipped carrier assembly 120 of FIG. 6 as well as a second insertable shaft assembly. The second insertable shaft assembly preferably includes a different carrier assembly of ablation elements such as a different pattern of electrodes or electrodes with different properties that the first insertable shaft assembly. Electrode or other ablation element variations include but are not limited to: type of energy delivered; size; cross sectional geometry; cooling properties; heating properties; and combinations thereof. In another preferred embodiment of the kit, a catheter configured for creating lesions at or near the pulmonary veins of the left atrium is included.

Also depicted in FIG. 4 is a system of the present invention, including in addition to ablation catheter 100, RF delivery unit 200, an interface unit of the present invention which connects to handle 110 with a multi-conductor cable 202 at RF attachment port 181. RF delivery unit 200 includes user interface 201, such as a user interface including data input devices like touch screens, buttons, switches, keypads, magnetic readers and other input devices; and also including data output devices like data and image screens, lights, audible transducers, tactile transducers and other output devices. User interface 201 is used to perform numerous functions including but not limited to: selecting electrodes to receive energy (electrodes 130 of carrier assembly 120); setting power levels, types (bipolar and monopolar) and durations; setting catheter and other system threshold levels; setting mapping and other system parameters; initiating and ceasing power delivery; deactivating an alarm condition; and performing other functions common to electronic medical devices. User interface 201 also provides information to the operator including but not limited to: system parameter information including threshold information; mapping and ablation information including ablation element temperature and cooling information; and other data common to ablation therapy and other electronic medical devices and procedures. In a preferred embodiment, RF delivery unit 200 attaches to a temperature probe, such as an esophageal temperature probe, determines the temperature from one or more sensors integral to the probe, and further interprets and/or displays the temperature information on user interface 201. In another preferred embodiment, RF delivery unit 200 also includes cardiac mapping means, such that mapping attachment port 182 can be attached to RF delivery unit 200 avoiding the need for a separate piece of equipment in the system. In another preferred embodiment, RF delivery unit 200 can also deliver ultrasound and/or another form of energy, such energy delivered by one or more additional ablation elements integral to carrier assembly 120, additional ablation elements not shown. Applicable types of energy include but are not limited to: sound energy such as acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof.

In a preferred embodiment, ablation catheter 100 includes an embedded identifier (ID), an uploadable electronic or other code, which can be used by RF delivery unit 200 to confirm compatibility and other acceptability of the specific catheter 100 with the specific RF delivery unit 200. The electronic code can be a bar code, not shown, on handle 110 which is read by RF delivery unit 200, an electronic code which is transferred to RF delivery unit 200 via a wired or wireless connection, not shown, or other identifying means, such as an RF tag embedded in handle 110. In another preferred embodiment, RF delivery unit 200 also includes an embedded ID, such as an ID that can be downloaded to catheter 100 for a second or alternative acceptability check. The embedded ID can also be used to automatically set certain parameters or certain parameter ranges, and can be used to increase safety by preventing inadvertent settings outside of an acceptable range for the specific catheter 100.

Handle 110 includes two push buttons, first button 116 and second button 117. These buttons can be used to perform one or more functions, and can work in cooperation with user input components of user interface 201 such that commands entered into user interface 201 set the action taken when either or both button 116 and button 117 are pressed. In a preferred embodiment, both button 116 and button 117 must be pressed simultaneously to deliver energy to one or more ablation elements of catheter 100. At the distal end of catheter shaft 101 is a circumferential band, band 104. Band 104 is preferably a visualization marker, such as a radiographic marker, ultrasound marker, electromagnetic marker, magnetic marker and combinations thereof. In an alternative embodiment, band 104 transmits or receives energy, such as when the marker is used as a ground or other electrode during an ablation. In another alternative embodiment, band 104 is an antenna used to determine the position of the distal end of catheter shaft 101 or the location of another component in relation to band 104. In another preferred embodiment, band 104 is used to store energy, such as capacitively stored energy that can be used to generate a magnetic field or to deliver ablation energy.

While the ablation catheter of FIGS. 4 and 4a is shown with an umbrella tip geometry, it should be appreciated that numerous configurations of carrier arms, such as spiral, zig-zag, and other patterns could be employed. These carrier assemblies are configured to provide sufficient forces to maximally engage the appropriate ablation element with the tissue to be ablated, without adversely impacting neighboring structures and other tissues. While the carrier assembly 120 of FIG. 4 "folds in" during retraction of shaft 150, other collapsing configurations can be employed such as the "fold out" configuration of the catheter of FIG. 2a, or configuration in which the carrier assembly transforms from a spiral, zigzag, or other curvilinear shape to a relatively straight or linear configuration as it is retracted and captured by the lumen of catheter shaft 101. Electrodes 130 of carrier assembly of FIG. 4 are shown facing out from the distal end of shaft 101 such that advancement or "pushing" of carrier assembly 120 engages electrodes 130 with tissue. In an alternative embodiment, electrodes are positioned, alternatively or additionally, to face toward the distal end of shaft 101. These electrodes may be mounted to proximal arm segment 125 such that retraction or "pulling" of carrier assembly 120, once deployed, engages these rear facing electrodes with tissue.

Ablation catheter 100 and RF delivery unit 200 are configured to ablate tissue with minimal power and precise control. RF Power levels are preferably less than 10 watts per electrode, and preferably 3 to 5 watts. Electrodes 130 are powered to reach an ablation temperature of approximately 60° C. The electrode geometries of the present invention, described in detail in reference to FIGS. 5a through 5f and FIGS. 6a through 6c, provide numerous and varied benefits including enhanced cooling properties. Electrodes of the present invention are configured to transition from an ablation temperature of 60° C. to body temperature of 37° C. in less than 20 seconds and preferably less than ten seconds. These electrodes are further configured to increase from body temperature to ablation temperature in less than 5 seconds. In a preferred embodiment, bipolar RF energy is delivered subsequent to monopolar delivery. The electrodes and power delivery subsystems of the present invention are configured to allow the electrode and neighboring tissue to decrease in temperature during the bipolar RF energy delivery following the monopolar delivery. This bimodal, sequential power delivery reduces procedure time, allows precise control of lesion depth and width, and reduces large swings in ablation temperatures. In another preferred embodiment, the temperature in the tissue in proximity to the electrode actually continues to increase as the electrode temperature decreases, such as during the bipolar delivery following monopolar delivery. In an alternative embodiment, the monopolar delivery cycle, the bipolar delivery cycle, or both, are followed by a period of time in which no RF energy is delivered. During this "off" time period, no energy may be delivered or an alternative energy may be delivered such as cryogenic energy that actually decreases the temperature of the tissue in order to ablate.

In a preferred embodiment, parameters associated with the bipolar and monopolar energy delivery are adjusted during the procedure, automatically by the system and/or manually by the operator. The energy delivery parameters are adjusted by measured, calculated or otherwise determined values include those relating to: energy delivered measurements such as voltage or current delivered to an electrode; force or pressure measurement such as the force exerted by the carrier assembly as measured by an integral strain gauge; other ablation catheter or ablation system parameter; temperature of tissue; rate of change of temperature of tissue; temperature of an electrode or other ablation element; rate of change of temperature of an electrode or other ablation element; EKG; tissue thickness; tissue location; cardiac flow-rate; other patient physiologic and other patient parameters; and combinations thereof. The energy delivery drive parameters may be adjusted by a combination of these determined values. In order to automatically modify an energy delivery parameter, or to notify an operator of a condition, these determined values are compared to a threshold, such as via a threshold comparator integral to the interface unit of the present invention. Threshold values can be calculated by the system or can be entered by the operator into a user interface of the system.

Energy delivered measurements, such as current, voltage and power measurements, which may be compared to a threshold value, include average energy; instantaneous energy; peak energy; cumulative or integrated energy amounts; and combinations thereof. In the catheter and system of the present invention, average power is approximately 5 Watts and less, cumulative energy for a cycle of bipolar and monopolar delivery is typically less than 500 Watt-seconds and preferably less than 300 Watt-seconds (5 watts for 60 seconds). Each threshold value may change over time and may be adjustable by an operator such as via a password enabled user interface. Cumulative determined values, such as cumulative energy delivered and "time at temperature" values may be able to be reset, such as automatically by the system and/or manually by an operator. Automatic resets may occur at specific events such as each time an ablation element is repositioned on tissue or each time energy delivered changes states, including the switching of electrodes receiving energy or the completion of a monopolar-bipolar delivery cycle.

Determined values such as temperature measurements may be made from single or multiple sensors, such as multiple temperature sensors during a single ablation cycle. In a preferred embodiment, multiple sensors are used and the more extreme (e.g. a higher temperature) value is compared to a threshold. When the threshold comparator determines a particular threshold has been reached, the system can adjust or otherwise react in various ways. In a preferred embodiment, the system enters an alarm or alert state. In another preferred embodiment, the energy delivery transmitted to an ablation element is modified; such as to cease or reduce the amount of RF energy delivered to an electrode. Numerous energy delivery parameters can be modified including but not limited to: current level; voltage level; frequency (usually fixed at 500 KHz); bipolar delivery "on" times; monopolar delivery "on" times; no energy delivery "on" times; electrode selected such as bipolar return electrode selected; and combinations thereof.

The automatic and manual adjustments of the present invention are triggered by comparing a measured, calculated or otherwise determined value to a threshold. These adjustments improve numerous outcomes of the proposed ablation therapy including those associated with improved efficacy and reduced adverse events. Specific benefits include precision controlled depth and width of lesions through a combination of bipolar and monopolar sequential duty cycles. The system is adjustable by the operator to modify intended lesion geometry to safely avoid structures like pulmonary vein lumens and the esophagus, as well as work in portions of the atrial wall that require deep lesions to effectively interrupt aberrant pathways.

Referring now to FIGS. 5a through 5f, multiple preferred embodiments of electrode-type ablation element of the present invention are illustrated. These electrodes are shown in sectional view in contact with tissue 30 just prior to or during delivery of energy to tissue 30 via the electrode. Each of the electrodes of FIGS. 5a through 5f are intended to maximize cooling, minimize energy delivered to non-targeted tissue (e.g. blood), or both. Certain electrodes are configured to minimize "low flow" areas for blood, such blood more likely to absorb enough energy to clot during an energy delivery cycle. The electrode cross sections assume various geometries such as triangular, semi-circular and crescent shaped, and are all preferably relatively uniform along their length such as to simplify their manufacturing. Cross sectional geometries are configured to create lesions of specific widths and depths, and to otherwise minimize trauma to neighboring tissue such as when force is applied to press the electrode "into" the tissue to be ablated. In a preferred embodiment, each of the electrodes of FIGS. 5a through 5f includes one or more temperature sensors, such as a thermocouple in a non-energy delivery portion.

Figure 5A:
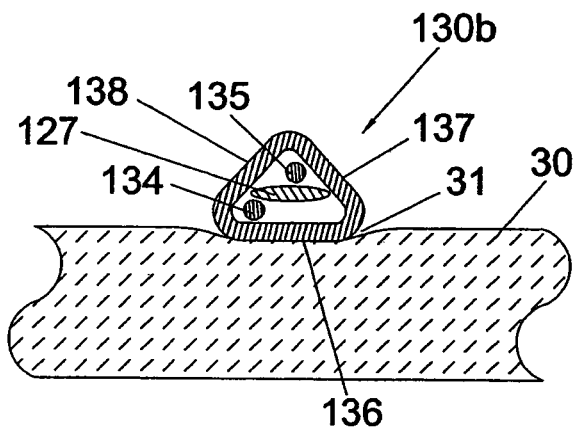
FIGS. 5a, 5b, 5c, 5d, 5e, and 5f are sectional end views of ablation elements consistent with the present invention, shown in associated contact with tissue during energy delivery.

Referring specifically to FIG. 5a, electrode 130b is displayed including a triangular cross section and configured to be placed by an operator with base 136 in contact with tissue 30. Electrode 130b includes an isosceles triangle cross section, with two equal sides, sides 137 and 138, each positioned in circulating blood when ablation energy, such as RF energy, is being delivered via wires 134 and 135. Electrode 130b is fixedly mounted to distal arm segment 127, as has been described in detail in reference to previous figures. Distal arm segment 127 is sufficiently rigid to allow the operator to apply a force to electrode 130b such that electrode 130b can be pressed, as shown, into tissue 30. The transition point from base 136 to side 137 and from base 136 to side 138 each are rounded such that although electrode 130b is slightly depressed into tissue 30, low blood flow area 31 (an area where blood will tend to heat up at a faster rate) is minimized as well as tension in the neighboring tissue. The surface area of sides 137 and 138 are sufficiently large (i.e. the combined lengths of sides 137 and 138 is sufficiently long) such that their combined surface area is greater than 60% of the overall total surface area of electrode 130b, preferably greater than 75% of the total. This high percentage of surface area in the circulating blood provides rapid and efficient cooling of electrode 130b.

Figure 5B:
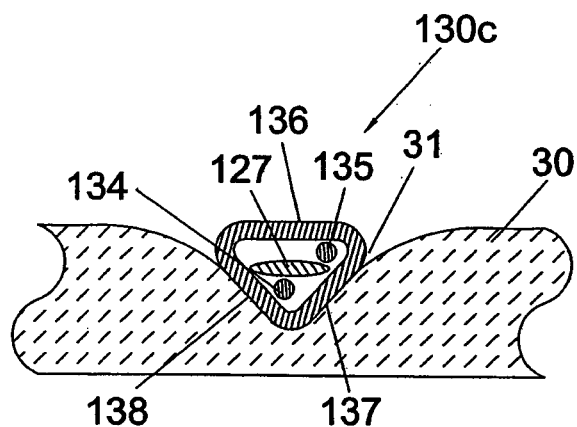

Referring specifically to FIG. 5b, electrode 130c is displayed including a triangular cross section and configured to be placed by an operator with the majority of sides 137 and 138 in contact with tissue 30. Electrode 130c includes an isosceles triangle cross section and base 136 positioned in circulating blood when ablation energy, such as RF energy, is being delivered via wires 134 and 135. Electrode 130c is fixedly mounted to distal arm segment 127, as has been described in detail in reference to previous figures. Distal arm segment 127 is sufficiently rigid to allow the operator to apply a force to electrode 130c such that electrode 130c can be pressed, as shown, into tissue 30. The surface area of sides 137 and 138 are sufficiently large such that their combined surface area is greater than 60% of the overall total surface area of electrode 130c, preferably greater than 70% of the total. This high percentage of surface area in contact with tissue minimizes the amount of energy delivered by electrode 130c into the neighboring blood. The energy delivery parameters are chosen such as to prevent the blood residing in or near low flow area 31 from clotting.

Figure 5C:
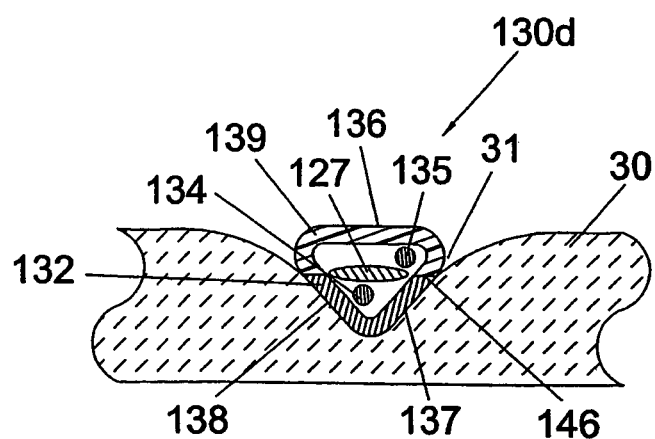

Referring specifically to FIG. 5c, electrode 130d is displayed including a laminate construction with a triangular cross section and configured to be placed by an operator with the majority of sides 137 and 138 in contact with tissue 30. Electrode 130d is configured to both improve cooling, and maximize energy delivered to tissue versus blood. Electrode 130d includes an isosceles triangle cross section, with base 136 positioned in circulating blood when ablation energy, such as RF energy, is being delivered via wires 134 and 135. Electrode 130d is fixedly mounted to distal arm segment 127, as has been described in detail in reference to previous figures. Distal arm segment 127 is sufficiently rigid to allow the operator to apply a force to electrode 130d such that electrode 130d can be pressed, as shown, into tissue 30. Electrode 130d has a laminate construction that includes a first portion that receives and delivers energy to tissue, electrical portion 132, a segment preferably constructed of standard RF electrode materials described hereinabove. Electrical portion 132 makes up the majority of sides 137 and 138 and is sized such that all or nearly all of its surface area is in contact with tissue 30 during delivery of energy. Electrode 130d has a second portion that is thermally conductive, thermal portion 139. Thermal portion 139 is either electrically non-conductive, minimally electrically conductive, and/or electrically isolated from electrical portion 132 such that thermal portion 139 does not deliver energy when energy is applied to and delivered by electrical portion 132. Thermal portion 139 may be constructed of standard electrode materials but be electrically isolated from electrical portion 132 such as with insulating glue 146. In this configuration and in an additional embodiment, thermal portion 139 may also (in addition to electrical portion 132) independently be used to map or deliver energy with different drive wires not shown. Alternatively, thermal portion 139 may be a plastic with high thermal conductivity such as a Konduit™ thermally conductive thermoplastic compound manufactured by LNP Engineering Plastics of Exton, Pa. Thermal portion 139 makes up a small portion of each of side 137 and side 138, and the entirety of base 136 such that when electrode 130d is positioned "into" tissue by the operator, most of thermal portion 139 is in the circulating blood, dissipating heat from electrical portion 132 and the neighboring tissue. Thermal portion 139 is sized such that no significant energy is delivered to low flow area 31, greatly reducing any chance of clot formation. Electrode 130d is configured to apply the great majority of the energy it receives into tissue and not blood, as well as provide enhanced cooling by having a thermal portion with significant surface area and/or efficient thermal mass that resides in the circulating blood during energy delivery. In an alternative embodiment, thermal portion 139 further includes a projecting fin to increase the transfer of heat from electrode 130d into the blood stream as has been described in reference to FIG. 2b hereinabove. In an alternative embodiment, not shown, electrode 130d is fixedly attached to distal arm segment 127 in the opposite (mirrored) orientation such that base 136 is in contact with tissue 30 during ablation, similar to the attachment configuration of electrode 130b of FIG. 5a. In this particular preferred embodiment, electrical portion 132 makes up the majority of base 136, and thermal portion 139 makes up both sides 137 and 138 as well as two small end portions of base 136, such that all of the energy delivered from base 136 is transferred to tissue 30, and a greatly increased surface area comprising sides 137 and 138 is in contact with circulating blood to cool electrode 130d.

Figure 5D:
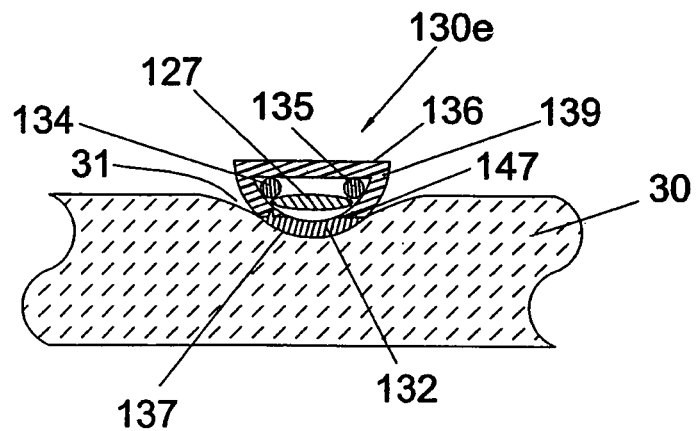

Referring specifically to FIG. 5d, electrode 130e is displayed including a similar construction to electrode 130d of FIG. 5c with a semi-circular cross section instead of a triangular cross section and a portion which does not deliver energy but acts as a heat sink. The crescent shaped cross section of electrode 130e causes less tissue deflection per unit force than the triangular cross section of electrode 130d of FIG. 5c, and may be preferable for ablating a wider lesion, ablating in areas of thin or weakened tissue, or for other operator preferences or patient requirements. Electrode 130e is configured to be placed by an operator with a central portion of rounded side 137 in contact with tissue 30. Electrode 130e is configured to both improve cooling, and maximize energy delivered to tissue versus blood. Base 136 is positioned in circulating blood when ablation energy, such as RF energy, is being delivered via wires 134 and 135. Electrode 130e is fixedly mounted to distal arm segment 127, as has been described in detail in reference to previous figures. Distal arm segment 127 is sufficiently rigid to allow the operator to apply a force to electrode 130e such that electrode 130e can be pressed, as shown, into tissue 30. Electrode 130e has a laminate construction that includes a first portion that receives and delivers energy to tissue, electrical portion 132, a segment preferably constructed of standard RF electrode materials described hereinabove. Electrical portion 132 is sized such that all or nearly all of its surface area is in contact with tissue 30 during delivery of energy. Electrode 130e has a second portion that is thermally conductive, thermal portion 139. Thermal portion 139 is either electrically non-conductive or electrically isolated from electrical portion 132 such that thermal portion 139 does not deliver energy when energy is applied to and delivered by electrical portion 132. Thermal portion 139 is a plastic with high thermal conductivity such as a Konduit™ thermally conductive thermoplastic compound manufactured by LNP Engineering Plastics of Exton, Pa. and is attached to electrical portion 132 at joint 147. Alternatively, thermal portion 139 may be constructed of standard electrode materials and be electrically isolated from electrical portion 132 such as with insulating glue, not shown. Thermal portion 139 is appropriately sized such that when the operator positions electrode 130d into tissue, most of thermal portion 139 is in the circulating blood, efficiently dissipating heat from electrical portion 132 and the neighboring tissue. Thermal portion 139 is sized such that no significant energy is delivered to low flow area 31, greatly reducing any chance of clot formation. Electrode 130e is configured to apply the great majority of the energy it receives into tissue and not blood, as well as provide enhanced cooling by having a thermal portion with significant surface area and/or efficient thermal mass that resides in the circulating blood during energy delivery. In an alternative embodiment, thermal portion 139 further includes a fin to increase the transfer of heat from electrode 130e into the blood stream.

Figure 5E:
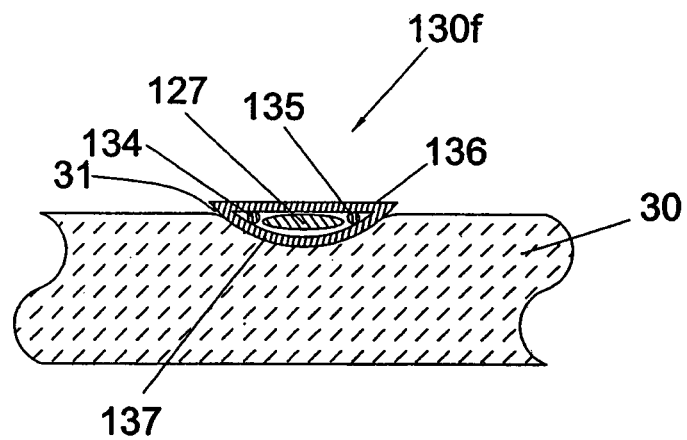

Referring specifically to FIG. 5e, electrode 130f is displayed including a crescent shaped cross section and configured to be placed by an operator with side 137 in contact with tissue 30. The crescent shaped cross section of electrode 130f causes less tissue deflection per unit force than the triangular cross section of electrode 130d of FIG. 5c, and may be preferable for ablating a wider lesion, ablating in areas of thin or weakened tissue, or for other operator preferences or patient requirements. The surface area of base 136, positioned in circulating blood when ablation energy is being delivered via wires 134 and 135, is less that the surface area of side 137, which causes the majority of energy delivered to electrode 130*f* to be delivered to tissue versus blood. The crescent shape of electrode 130*f* is chosen to minimize trauma as electrode 130*f* is being pressed into the tissue. Electrode 130*f* is fixedly mounted to distal arm segment 127, as has been described in detail in reference to previous figures. Distal arm segment 127 is sufficiently rigid to allow the operator to apply a force to electrode 130*f* such that electrode 130*f* can be pressed, as shown, into tissue 30. The crescent shape greatly reduces the volume of low flow area 31, minimizing the chance of blood clotting.

Figure 5F:
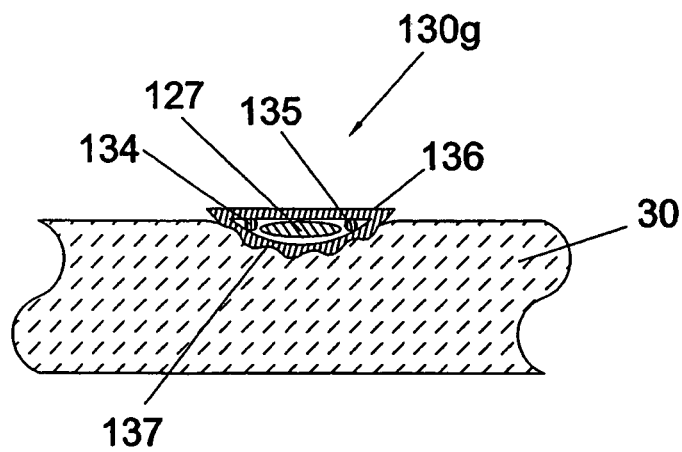

Referring specifically to FIG. 5*f*, electrode 130*g* is displayed including a crescent shaped cross section and configured to be placed by an operator with side 137 in contact with tissue 30. The crescent shaped cross section of electrode 130*g* causes less tissue deflection per unit force than the triangular cross section of electrode 130*d* of FIG. 5*c*, and may be preferable for ablating a wider lesion, ablating in areas of thin or weakened tissue, or for other operator preferences or patient requirements. As compared to electrode 130*f* of FIG. 5*e*, side 137 has a serpentine segment that greatly increases the surface area of side 137. In should be appreciated that numerous other configurations can be used to increase the length of side 137 and the resultant surface area, such as zigzag segments and combinations of straight and non-straight line segments. The surface area of base 136, positioned in circulating blood when ablation energy is being delivered via wires 134 and 135, is much less that the surface area of side 137, which causes a great majority of energy delivered to electrode 130*g* to be delivered to tissue versus blood. The crescent shape of electrode 130*g* is chosen to minimize trauma as electrode 130*f* is being pressed into the tissue. Electrode 130*g* is fixedly mounted to distal arm segment 127, as has been described in detail in reference to previous figures. Distal arm segment 127 is sufficiently rigid to allow the operator to apply a force to electrode 130*g* such that electrode 130*g* can be pressed, as shown, into tissue 30. The crescent shape greatly reduces the volume of low flow area 31, minimizing the chance of blood clotting. In an alternative embodiment, electrode 130*g* is fixedly mounted to distal arm segment 127 in the opposite (mirrored) orientation such that the large surface area serpentine side 137 is in the circulating blood during ablation, providing a highly efficient cooling electrode configuration.

Figure 6A:
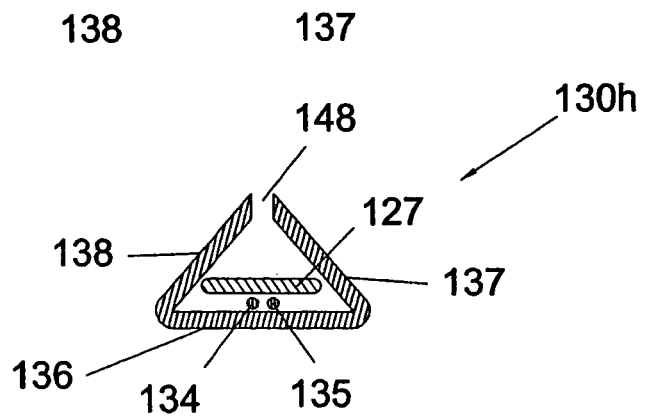
FIGS. 6a and 6b are sectional end views of ablation elements consistent with the present invention.
Figure 6B:
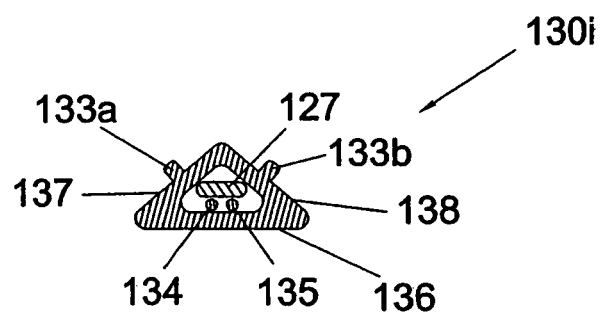
Figure 6C:
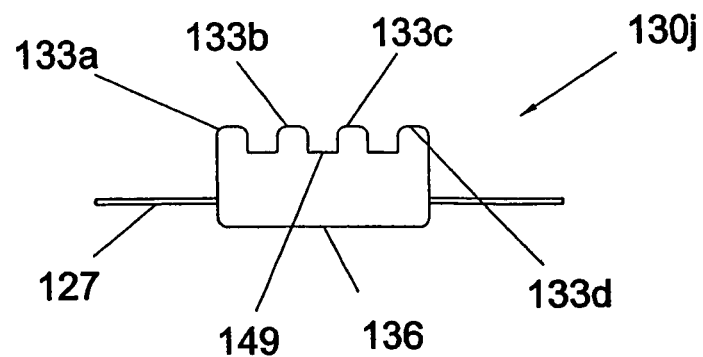
FIG. 6c is a side view of an ablation element consistent with the present invention.

Referring now to FIGS. 6*a* through 6*cf*, multiple preferred embodiments of electrode-type ablation element of the present invention are illustrated. Each of the electrodes of FIGS. 6*a* through 6*c* are intended to maximize cooling, minimize energy delivered to non-targeted tissue (e.g. blood), or both. Certain electrodes are configured to minimize "low flow" areas for blood, such blood more likely to absorb enough energy to clot during an energy delivery cycle. The electrodes cross sections assume various geometries and are all preferably relatively uniform along their length such as to simplify their manufacturing. Cross sectional geometries are configured to create lesions of specific widths and depths, and to otherwise minimize trauma to neighboring tissue such as when force is applied to press the electrode "into" the tissue to be ablated. In a preferred embodiment, each of the electrodes of FIGS. 6*a* through 6*c* includes one or more temperature sensors, such as a thermocouple in a non-energy delivery portion.

Referring specifically to FIG. 6*a*, electrode 130*h*, displayed in a sectional view, has a triangular cross section and is configured to be placed by an operator with base 136 in contact with tissue to be ablated. Electrode 130*h* includes an isosceles triangle cross section, with two equal sides, sides 137 and 138, each positioned in circulating blood when ablation energy, such as RF energy, is being delivered via wires 134 and 135. Electrode 130*h* is fixedly mounted to distal arm segment 127, as has been described in detail in reference to previous figures. Distal arm segment 127 is sufficiently rigid to allow the operator to apply a force to electrode 130*h* such that electrode 130*h* can be pressed into the tissue to be ablated. The transition point from base 136 to side 137 and from base 136 to side 138 each are rounded to reduce tissue trauma and low blood flow areas during ablation. The thickness of sides 137 and 138 as well as base 136 are chosen to have sufficient mass to effectively deliver energy to tissue without overheating, while minimizing a large thermal mass that would be difficult to cool. In a preferred embodiment, sides 137 and 138 have a smaller wall thickness than base 136, differentiation in thickness not illustrated. Side 137 and side 138 are not connected, leaving opening 148 opposite side 136, to provide enhanced cooling such as by increasing the effective surface area (allowing circulating blood to pass by the interior surfaces of sides 137 and 138 and potentially base 136). The surface area of sides 137 and 138 are sufficiently large (i.e. the combined lengths of sides 137 and 138 is sufficiently long) such that their combined surface area is greater than 60% of the overall total surface area of electrode 130*h*, preferably greater than 75% of the total. In alternative embodiments, side 137 and/or side 138 comprises a non-straight segment such as a curved segment, serpentine segment, zigzag segment, or combinations of straight and non-straight segments. The high percentage of surface area in the circulating blood, in addition to the advantages provided by opening 148, provide rapid and efficient cooling of electrode 130*h*.

Referring specifically to FIG. 6*b*, electrode 130*i*, displayed in a sectional view, has a triangular cross section and is configured to be placed by an operator with base 136 in contact with tissue to be ablated. Electrode 130*i* includes an isosceles triangle cross section, with two equal sides, sides 137 and 138, each positioned in circulating blood when ablation energy, such as RF energy, is being delivered via wires 134 and 135. Electrode 130*i* is fixedly mounted to distal arm segment 127, as has been described in detail in reference to previous figures. Distal arm segment 127 is sufficiently rigid to allow the operator to apply a force to electrode 130*i* such that electrode 130*i* can be pressed into the tissue to be ablated. The transition point from base 136 to side 137 and from base 136 to side 138 each are rounded to reduce tissue trauma and low blood flow areas during ablation. The thickness of sides 137 and 138 as well as base 136 are chosen to have sufficient mass to effectively deliver energy to tissue without overheating, while minimizing a large thermal mass that would be difficult to cool. In a preferred embodiment, sides 137 and 138 have a smaller wall thickness than base 136, differentiation in thickness not illustrated. Side 137 and side 138 are not connected, leaving opening 148 opposite side 136, to provide enhanced cooling such as by increasing the effective surface area (allowing circulating blood to pass by the interior surfaces of sides 137 and 138 and potentially base 136). Included on each of side 137 and side 138 is a projecting fin, fin 133*a* and 133*b* respectively, which increase the surface areas of sides 137 and 138. The surface areas of sides 137 and 138 are sufficiently large (i.e. the combined lengths of sides 137 and 138 is sufficiently long) such that their combined surface area is greater than 60% of the overall total surface area of electrode 130*i*, preferably greater than 75% of the total. The high percentage of surface area in the circulating blood provides rapid and efficient cooling of electrode 130i.

Referring specifically to FIG. 6c, electrode 130j, displayed in a side view, is configured to be placed by an operator with base 136 in contact with tissue to be ablated. Electrode 130j includes a rectangular cross-section, not illustrated, with four projecting fins 133a, 133b, 133c and 133d extending from atop surface 149. Top surface 149 and each projecting fin are each positioned in circulating blood when ablation energy, such as RF energy, is being delivered via wires 134 and 135. Electrode 130j is fixedly mounted to distal arm segment 127, as has been described in detail in reference to previous figures. Distal arm segment 127 is sufficiently rigid to allow the operator to apply a force to electrode 130j such that electrode 130j can be pressed into the tissue to be ablated. The thickness of base 136, top surface 149 and projections 133a, 133b, 133c and 133d are chosen to have sufficient mass to effectively deliver energy to tissue without overheating, while minimizing a large thermal mass that would be difficult to cool. In a preferred embodiment, top surface 149 and fins 133a, 133b, 133c, and 133d have a smaller wall thickness than base 136, differentiation in thickness not illustrated. The surface areas of top surface 149 and fins 133a, 133b, 133c and 133d are sufficiently large such that their combined surface area is typically greater than 60% of the overall total surface area of electrode 130i, preferably greater than 85% of the total. The high percentage of surface area in the circulating blood provides rapid and efficient cooling of electrode 130j.

It should be understood that numerous other configurations of the systems, devices and methods described herein may be employed without departing from the spirit or scope of this application. The ablation catheter includes one or more ablation elements such as the electrodes described in reference to FIGS. 5a through 5f and FIGS. 6a through 6c. These electrodes include various cross-sectional geometries, projecting fins, energy delivering portions and non-energy delivering portions, and other features described in reference to these drawings. It should be appreciated that one or more features described in reference to one specific electrode can be combined with one or more features described in reference to a different electrode, in whole or in part, in any combination, without departing from the spirit and scope of this application. The electrodes can be configured to maximize tissue contact of the energy delivering portion(s), maximize cooling, or both. Clinician preferences, broad patient population requirements, and other treatment goals are likely to require catheters with different performance parameters, as are described in detail throughout this application, to both safely and effectively block an aberrant conductive pathway. The systems, catheters and ablation elements of the present invention are designed to achieve specific depths and widths of lesions, while preventing overheating that may damage more tissue than necessary and/or create dangerous embolus such as blood clots or fragmented tissue. The systems of the present invention are configured to automatically, semi-automatically or manually adjust the energy applied to the ablation elements such as by adjusting one or more of the following: the level or amount of energy delivered; type of energy delivered; drive signal supplied such as monopolar and bipolar; phasing, timing or other time derived parameter of the applied energy; and combinations thereof.

The ablation elements of the present invention are attached to energy delivery conduits that carry the energy to the electrode that is supplied by the interface unit. RF electrodes are connected to wires, preferably in a configuration with individual wires to at least two electrodes to allow independent drive of the electrodes including sequential and simultaneous delivery of energy from multiple electrodes. Alternative or additional energy delivery conduits may be employed, such as fiber optic cables for carrying light energy such as laser energy; tubes that carry cryogenic fluid for cryogenic ablation or saline for saline mediated electrical energy ablation; conduits for carrying sound energy; other energy delivery conduits; and combinations thereof.

The system includes multiple functional components, such as the ablation catheter, and the interface unit. The interface unit preferably energy supply means and a user interface, as well as calculating means for interpreting data such as mapping data and data received from one or more sensors, as well as means of comparing measured, calculated or otherwise determined values to one or more thresholds. In a preferred embodiment, a low level energy delivery is performed prior to a higher level energy delivery. During or after the low energy delivery, one or more parameters are measured, calculated or otherwise determined that are used to determine a threshold for the second energy delivery, such as a second delivery of energy to the same relative tissue location.

The interface unit further includes means of adjusting one or more system parameters, such as the amount type, or configuration of energy being delivered, when a particular threshold is met. The ablation catheter includes at least one ablation element for delivering energy to tissue such as cardiac tissue. Cardiac tissue applicable for ablation includes left and right atrial walls, as well as other tissues including the septum and ventricular tissue. The ablation catheter of the present invention includes a flexible shaft with a proximal end, a distal end, and a deployable carrier assembly with at least one, and preferably multiple ablation elements. The flexible shafts may include one or more lumens, such as thru lumens or blind lumens. A thru lumen may be configured to allow over-the-wire delivery of the catheter or probe. Alternatively the catheter may include a rapid exchange sidecar at or near its distal end, consisting of a small projection with a guidewire lumen therethrough. A lumen may be used to slidingly receive a control shaft with a carrier assembly on its distal end, the carrier assembly deployable to exit either the distal end or a side hole of the flexible shaft. The advancement of the carrier assembly, such as through a side hole, via controls on the proximal end of the device, allows specific displacement of any functional elements, such as electrodes, mounted on the carrier assembly. Other shafts may be incorporated which act as a rotational linkage as well as shafts that retract, advance or rotate one or more components. A lumen may be used as an inflation lumen, which permits a balloon mounted on a portion of the exterior wall of the flexible shaft to be controllably inflated and deflated. The balloon may be concentric or eccentric with the central axis of the shaft, it may be a perfusion balloon, and may include an in-line pressure sensor to avoid over-pressurizing. A lumen may be used to receive a rotating linkage, such as a linkage used to provide high-speed rotation of an array of ultrasound transducers mounted near the distal end of the linkage. Each device included in a lumen of the flexible shafts may be removable or configured to prevent removal.

The ablation catheter of the present invention may include one or more functional elements, such as one or more location elements, sensors, transducers, antennas, or other functional components. Functional elements can be used to deliver energy such as electrodes delivering energy for tissue ablation, cardiac pacing or cardiac defibrillation. Functional elements can be used to sense a parameter such as tissue temperature; cardiac signals or other physiologic parameters; contact with a surface such as the esophageal or atrial walls of a patient; an energy parameter transmitted from another functional element such as amplitude, frequency; phase; direction; or wavelength parameters; and other parameters. In a preferred embodiment of the present invention, the ablation catheter includes multiple functional elements. In another preferred embodiment, the ablation catheter includes a deflectable distal end; such as a deflected end that causes one or more functional elements to make contact with tissue. Deflection means may include one or more of: a pull wire; an expandable cage such as an eccentric cage; an expandable balloon such as an eccentric balloon; an expandable cuff; a deflecting arm such as an arm which exits the flexible catheter shaft in a lateral direction; and a suction port.

The ablation catheter of the present invention preferably includes a handle on their proximal end. The handle may be attached to an outer sheath, allowing one or more inner shafts or tubes to be controlled with controls integral to the handle such as sliding and rotating knobs that are operable attached to those shafts or tubes. Alternatively, the handle may be attached to a shaft that is slidingly received by an outer sheath, such that an operator can advance and retract the shaft by advancing and retracting the handle and holding the sheath in a relatively fixed position. The handle may include one or more attachment ports, such as attachment ports which electrically connect to one or more wires; ports which provide connection to optical fibers providing laser or other light energies; ports which fluidly connect to one or more conduits such as an endoflator for expanding a balloon with saline or a source of cooling fluids; and combinations thereof. Other controls may be integrated into the handle such as deflecting tip controls, buttons that complete a circuit or otherwise initiate an event such as the start of energy delivery to an ablation element. In addition, the handle may include other functional components including but not limited to: transducers such as a sound transducer which is activated to alert an operator of a change is status; a visual alert component such as an LED, a power supply such as a battery; a lock which prevents inadvertent activation of an event such as energy delivery; input and output devices that send and receive signals from the interface unit of the present invention; and combinations thereof.

The interface unit of the present invention provides energy to the ablation elements of the ablation catheter. In preferred embodiments, one or more ablation elements are electrodes configured to deliver RF energy. Other forms of energy, alternative or in addition to RF, may be delivered, including but not limited to: acoustic energy and ultrasound energy; electromagnetic energy such as electrical, magnetic, microwave and radiofrequency energies; thermal energy such as heat and cryogenic energies; chemical energy; light energy such as infrared and visible light energies; mechanical energy; radiation; and combinations thereof. The ablation elements can deliver energy individually, in combination with or in serial fashion with other ablation elements. The ablation elements can be electrically connected in parallel, in series, individually, or combinations thereof. The ablation catheter may include cooling means to prevent undesired tissue damage and/or blood clotting. The ablation elements may be constructed of various materials, such as plates of metal and coils of wire for RF or other electromagnetic energy delivery. The electrodes can take on various shapes including shapes used to focus energy such as a horn shape to focus sound energy, and shapes to assist in cooling such as a geometry providing large surface area. Electrodes can vary within a single carrier assembly, such as a spiral array of electrodes or an umbrella tip configuration wherein electrodes farthest from the central axis of the catheter have the largest major axis. Wires and other flexible energy delivery conduits are attached to the ablation elements, such as electrical energy carrying wires for RF electrodes or ultrasound crystals, fiber optic cables for transmission of light energy, and tubes for cryogenic fluid delivery.

The ablation elements requiring electrical energy to ablate require wired connections to an electrical energy power source such as an RF power source. In configurations with large numbers of electrodes, individual pairs of wires for each electrode may be bulky and compromise the cross-sectional profile of the ablation catheter. In an alternative embodiment, one or more electrodes are connected in serial fashion such that a reduced number of wires, such as two wires, can be attached to two or more electrodes and switching or multiplexing circuitry are included to individually connect one or more electrodes to the ablative energy source. Switching means may be a thermal switch, such that as a first electrodes heats up, a single pole double throw switch change state disconnecting power from that electrode and attaching power to the next electrode in the serial connection. This integral temperature switch may have a first temperature to disconnect the electrode, and a second temperature to reconnect the electrode wherein the second temperature is lower than the first temperature, such as a second temperature below body temperature. In an alternative embodiment, each electrode is constructed of materials in their conductive path such that as when the temperature increased and reached a predetermined threshold, the resistance abruptly decreased to near zero, such that power dissipation, or heat, generated by the electrode was also near zero, and more power could be delivered to the next electrode incorporating the above switching means The interface unit of the present invention includes a user interface including components including but not limited to: an ultrasound monitor such as an ultrasound monitor in communication with one or more ultrasound crystals near a temperature sensor of an esophageal probe or ultrasound crystals within an electrode carrier assembly of the ablation catheter; an x-ray monitor such as a fluoroscope monitor used to measure the distance between two or more location elements; other user output components such as lights and audio transducers; input components such as touch screens, buttons and knobs; and combinations thereof. In a preferred embodiment, the interface unit provides functions in addition to providing the energy to the ablation catheter including but not limited to: providing a cardiac mapping function; providing cardiac defibrillation energy and control; providing cardiac pacing energy and control; providing a system diagnostic such as a diagnostic confirming proper device connection; providing the calculating function of the present invention; providing a signal processing function such as interpreting signals received from one or more sensors of a probe, such as an esophageal probe, and/or the ablation catheter; providing drive signals and/or energy to one or more functional elements of the ablation catheter; providing a second energy type to the ablation elements of the ablation catheter; and combinations thereof.

In a preferred embodiment, the interface unit provides an analysis function to determine one or more system parameters that correlate to ablation settings, the parameters including but not limited to: an energy delivery amount; an energy delivery frequency; an energy delivery voltage; an energy delivery current; an *energy delivery temperature; an energy delivery rate; an energy delivery duration; an energy delivery modulation parameter; an energy threshold; another energy delivery parameter; a temperature threshold; an alarm threshold; another alarm parameter; and combinations thereof. The analysis function compares a measured, calculated or otherwise determined function to a threshold value, such as a threshold value settable by an operator of the system. In a preferred embodiment, the interface unit receives temperature information from multiple sensors of the ablation catheter and/or other body inserted devices, and the highest reading received is compared to a temperature threshold such as a temperature threshold determined by the location of tissue being ablated. The analysis function includes one or more algorithms that mathematically process information such as signals received from sensors of the ablation catheter or other device; information entered into the user interface of the interface unit by the operator; embedded electronic information uploaded from the ablation catheter or other device such as information determined during the manufacture of the catheter or device; and combinations thereof. In a preferred embodiment, the ablation setting determined by the analysis function is provided to the operator via a display or other user interface output component.

The interface unit of the present invention performs one or more mathematical functions, signal processing functions; signal transmission functions; and combinations thereof, to determine a system performance (e.g. during ablation) or other system parameter. A calculation may include a function performed by an operator of the system such as a distance value that is entered into the interface unit after a measurement is performed such as a measurement made from an IVUS monitor or a fluoroscopy screen. In a preferred embodiment, energy delivered, such as a maximum cumulative energy, maximum peak energy or maximum average energy is limited by a threshold. In a preferred embodiment, when a temperature reaches a threshold, one or more system parameters are modified. These modifications include but are not limited to: a threshold parameter such as an increased temperature threshold; an alarm or alert parameter such as an audible alarm "on" state; an energy parameter such as a parameter changing energy type or modifying energy delivery such as switching from RF energy to cryogenic energy or stopping energy delivery; a sensor parameter such as a parameter which activates one or more additional sensors; cooling apparatus parameter such as a parameter activating a cooling apparatus; a parameter that changes the polarity of energy delivery or the modulation of energy delivery such as a parameter that switches from monopolar to bipolar delivery or phased monopolar-bipolar to bipolar; and combinations thereof.

The system of the present invention preferably includes multiple functional elements integral to the ablation catheter and/or other system component. These functional elements may be mounted on the outer wall of the flexible shaft of the device. Alternatively or additionally, one or more functional elements may be mounted to a balloon, such as a perfusion balloon, eccentric balloon or concentric balloon and/or elements may be mounted to a carrier assembly such as a carrier assembly than exits the distal end or a side hole of the flexible shaft. These functional elements may be covered with a membrane and multiple elements may be configured in an array such as an array that is rotated within a lumen of the flexible shaft. Functional elements may be placed on the patient's chest, such as EKG electrodes, pacing electrodes or defibrillation electrodes. Functional elements include but are not limited to: sensors such as temperature sensors; transmitters such as energy transmitting electrodes, antennas and electromagnetic transmitters; imaging transducers; signal transmitters such as drive signal transmitters.

Functional elements may include sensing functions such a sensor to detect a physiologic parameter. In a preferred embodiment, one or more functional elements are configured as sensors to receive signals that are indicative of one or more cardiac functions of the patient. Sensors may include but are not limited to: an electrical signal sensor such as a cardiac electrode; a temperature sensor such as a thermocouple; an imaging transducer such as an array of ultrasound crystals; a pressure sensor; a pH sensor; a blood sensor, a respiratory sensor; an EEG sensor, a pulse oximetry sensor; a blood glucose sensor; an impedance sensor; a contact sensor; a strain gauge; an acoustic sensor such as a microphone; a photodetector such as an infrared photodetector; and combinations thereof. Functional elements alternatively or additionally include one or more transducers. The transducer may be a location element; a transmitter such as a transmitting antenna, an RF electrode, a sound transmitter; a photodiode, a pacing electrode, a defibrillation electrode, a visible or infrared light emitting diode and a laser diode; a visualization transducer such as an ultrasound crystal; and combinations thereof.

Numerous kit configurations are also to be considered within the scope of this application. An ablation catheter is provided with multiple carrier assemblies. These carrier assemblies can be removed for the tubular body member of the catheter, or may include multiple tubular body members in the kit. The multiple carrier assemblies can have different patterns, different types or amounts of electrodes, and have numerous other configurations including compatibility with different forms of energy. Multiple sensors, such as EKG skin electrodes may be included, such as electrodes that attach to the interface unit of the present invention. A kit may include one or more catheters, such as an ultrasound catheter, which are configured to enter and extend distally in a lumen of the ablation catheter. One or more esophageal probes may be included such as probes with different tip or sensor configurations.

Though the ablation device has been described in terms of its preferred endocardial and percutaneous method of use, the array may be used on the heart during open-heart surgery, open-chest surgery, or minimally invasive thoracic surgery. Thus, during open-chest surgery, a short catheter or cannula carrying the carrier assembly and its electrodes may be inserted into the heart, such as through the left atrial appendage or an incision in the atrium wall, to apply the electrodes to the tissue to be ablated. Also, the carrier assembly and its electrodes may be applied to the epicardial surface of the atrium or other areas of the heart to detect and/or ablate arrhythmogenic foci from outside the heart.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth hereinbelow not be construed as being order-specific unless such order specificity is expressly stated in the claim.

What is claimed is:
1. An ablation catheter, comprising:
an elongate tube defining a lumen and having a distal end adapted for insertion into a patient;
at least one resilient arm having a constrained configuration inside the lumen and an expanded configuration outside the lumen;

at least one electrode disposed on the at least one resilient arm, the electrode comprising a tissue contact portion adapted to deliver energy to tissue and a circulating blood contact portion; and at least two projecting members extending from the circulating blood contact portion to provide rapid and efficient cooling of the electrode.

2. The catheter of claim 1 wherein the at least one electrode has a substantially triangular cross section.

3. The catheter of claim 2 wherein the substantially triangular cross section is an isosceles triangle.

4. The catheter of claim 2 wherein a vertex of the substantially triangular cross section is approximately 75 degrees.

5. The catheter of claim 2 further comprising a plurality of resilient arms and at least one electrode disposed on each arm, wherein the electrodes have a circular positioning in the constrained configuration.

6. The catheter of claim 2 wherein the electrode defines three surfaces, and the at least two projecting members extend from different surfaces.

7. The catheter of claim 1 wherein the projecting members further comprise fins.

8. The catheter of claim 1 wherein the projecting members comprise at least 60% of a total surface area of the at least one electrode.

9. The catheter of claim 1 wherein the projecting members comprise at least 70% of a total surface area of the at least one electrode.

10. The catheter of claim 1 wherein the at least one electrode has a surface area of less than approximately 2.5 mm$^2$.

11. The catheter of claim 1 wherein the at least one electrode has a volume of less than approximately 3.0 mm$^3$.

12. The catheter of claim 1 wherein the at least one electrode has a weight of less than approximately 0.05 grams.

13. The catheter of claim 1 wherein the projecting members enable rapid cooling of the at least one electrode from an ablation temperature to a body temperature in less than 20 seconds after an ablation cycle has ceased.

14. The catheter of claim 13 wherein the ablation temperature is approximately 60° C. and the body temperature is approximately 37° C.

15. The catheter of claim 1 wherein the projecting members enable rapid cooling of the at least one electrode from an ablation temperature to a body temperature in less than 10 seconds after an ablation cycle has ceased.

16. The catheter of claim 15 wherein the ablation temperature is approximately 60° C. and the body temperature is approximately 37° C.

17. The catheter of claim 1 wherein the at least one electrode is adapted to increase in temperature from a body temperature to an ablation temperature in less than 5 seconds.

18. The catheter of claim 17 wherein the ablation temperature is approximately 60° C. and the body temperature is approximately 37° C.

19. The catheter of claim 1 wherein the projecting members have an opening which enhances cooling of the at least one electrode by allowing circulating blood to pass within an interior of the at least one electrode.

20. An ablation catheter, comprising:
an elongate-tube defining a lumen and having a distal end adapted for insertion into a patient;
at least one resilient arm having a constrained configuration inside the lumen and an expanded configuration outside the lumen; and
at least one electrode disposed on the at least one resilient arm, the at least one electrode having:
an electrical tissue contact portion adapted to deliver energy to tissue,
a thermal dissipation portion electrically isolated and positioned away from the electrical portion and adapted to dissipate heat from the electrical portion into circulating blood, and
a fin projecting from the thermal dissipation portion.

21. The catheter of claim 20, further comprising a second fin projecting from the thermal portion.

22. The catheter of claim 20 wherein the at least one electrode has a substantially triangular cross section.

23. The catheter of claim 20 wherein the at least one electrode has a substantially semicircular cross section.

24. The catheter of claim 20 wherein a cross section of the at least one electrode has a curvilinear segment.

25. The catheter of claim 20 wherein a cross section of the at least one electrode has a serpentine segment.

26. The catheter of claim 20 wherein a cross section of the at least one electrode has a zigzag segment.

27. The catheter of claim 20 wherein the thermal portion comprises at least 60% of a total surface area of the at least one electrode.

28. The catheter of claim 20 wherein the thermal portion comprises at least 70% of a total surface area of the at least one electrode.

* * * * *